(12) United States Patent
Beaudry et al.

(10) Patent No.: US 7,070,991 B2
(45) Date of Patent: Jul. 4, 2006

(54) CELLS EXPRESSING A CD4-IGG2 CHIMERIC HETEROTETRAMER

(75) Inventors: Gary A. Beaudry, Upper Montclair, NJ (US); Paul J. Maddon, New York, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 365 days.

(21) Appl. No.: 08/485,163

(22) Filed: Jun. 7, 1995

(65) Prior Publication Data

US 2002/0098191 A1 Jul. 25, 2002

Related U.S. Application Data

(63) Continuation of application No. 07/960,440, filed as application No. PCT/US92/01143 on Feb. 10, 1992, now abandoned, which is a continuation-in-part of application No. 07/653,684, filed on Feb. 8, 1991, now abandoned.

(51) Int. Cl.
*C12N 5/10* (2006.01)
*C12N 15/12* (2006.01)
*C12N 15/63* (2006.01)

(52) U.S. Cl. .................. 435/325; 435/455; 435/252.3; 435/36.1; 530/350; 530/387.3; 536/23.1; 536/23.4; 536/23.5; 536/23.53

(58) Field of Classification Search ............... 530/350, 530/402, 387.3; 514/12; 536/23.4, 23.1, 536/23.53; 435/69.7, 252.3, 325, 358, 365, 435/320.1, 455; 424/134.1
See application file for complete search history.

(56) References Cited

U.S. PATENT DOCUMENTS

| 4,664,911 | A | | 5/1987 | Uhr et al. ............... 424/182.1 |
|---|---|---|---|---|
| 5,116,964 | A | * | 5/1992 | Capon et al. ................ 536/27 |
| 5,431,793 | A | * | 7/1995 | Wang et al. ............ 204/182.8 |
| 5,565,335 | A | * | 10/1996 | Capon et al. .............. 435/69.7 |
| 6,451,313 | B1 | * | 9/2002 | Maddon et al. .......... 424/185.1 |

FOREIGN PATENT DOCUMENTS

| EP | 0314317 | | 5/1989 |
|---|---|---|---|
| EP | 0394827 | | 10/1990 |
| WO | WO8801304 | | 2/1989 |
| WO | WO8901940 | | 3/1989 |
| WO | 8902922 | * | 4/1989 |
| WO | WO8903222 | | 4/1989 |
| WO | WO8906690 | | 7/1989 |
| WO | WO9001035 | | 2/1990 |
| WO | WO9100360 | | 1/1991 |
| WO | WO9213559 | | 8/1992 |

OTHER PUBLICATIONS

Capon et al. Nature 337:525-531 Feb. 9, 1989.*

Auffray, C., et al. (1991) CD-4 targeted immune intervention: a strategy for the therapy of AIDS and autoimmune disease, Tibtech vol. 9:124-131.
Byrn, R.A. et al. (1990) Biological properties of CD4 Immunoadhesin, Nature, vol. 344:667-670.
Chamow, S.M. et al. (1990) Enzymatic Cleavage of a CD4 Immunoadhesin generates Crystallized Biologically Active FD-Like Fragments, Biochemsitry, vol. 29, No. 42: 9885-9891.
Chowdhury, et al. (1991) Evaluation of anti-human Immunodeficiency Virus Affect of Recombinant CD4-Immunoglobin In-Vitro: A good candidate for AIDS treatment, Microbiol. Immunol., vol. 180, No. 4: 183-192.
Fahey, J.L. and Schooley, R. (1992) Status of immune-based therapies in HIV infection and AIDS, Clin exp. Immunol., vol. 88:1-5.
Maddon, et al. (1985) The isolation and Nucleotide Sequence of cDNA Encoding the T Cell Surface Protein T4: A new member of the Immunoglobin Gene Family, Cell, vol. 42: 93-104.
Morrison, S.L. et al. (1984) Chimeric Human Antibody Molecules: Mouse Antigen- binding domains with Human Constant Region Domains, Proc. Nat. Acad. Sci., vol. 81, 6851-6855.
Murray, J.L. et al. (1985) Radioimaging in Malignant Melanoma with "In-labeled Monoclonal Antibody 96.5" Cancer Research, vol. 45: 2376-2381.
Pastan, I. et al. (1989) Pseudomonas Exotoxin: Chimeric Toxins, J. Biological Chemistry, vol. 264, No. 26: 15157-15160.
Pastan, I. et al. (1991) Recombinant Toxins for Cancer Treatment, Science, vol. 254: 1173-1177.
Till, M.A. et al. (1988) HIV-Infected Cells are Killed by rCD4-Ricin A Chain, Science, vol. 242:1166-1168.
Traunecker, A. et al. (1989) Highly efficient Neutralization of HIV with Recombinant CD4-Immunoglobin Molecules, Nature, vol. 339: 68-70.
Zettmeissl, G. et al. (1990) Expression and Characterization of Human CD4: Immunoglobin Fusion Proteins, DNA and Cell Biology, vol. 9, No. 5:347-353.
Allaway Graham P. et al. (1993) Synergistic Inhibition of HIV-1 Envelope-Mediated Cell Fusion by CD4-Based Molecules in Combination with Anbodies to gp120 or gp41, AIDS Research and Human Retroviruses, vol. 11, No. 5, 533-539.
Capon, et al., (1989) "Designing CD4 Immunoadhesins For AIDS Therapy", Nature, vol. 337, pp. 525-531.

* cited by examiner

*Primary Examiner*—Phillip Gambel
(74) *Attorney, Agent, or Firm*—John P. White, Esq.; Cooper & Dunham LLP

(57) ABSTRACT

This invention provides an expression vector encoding a CD4-gamma2 chimeric heavy chain homodimer. This invention also provides an expression vector encoding the heavy chains of a CD4-IgG2 chimeric heterotetramer. Finally, this invention provides an expression vector encoding the light chains of a CD4-IgG2 chimeric heterotetramer.

9 Claims, 27 Drawing Sheets

FIGURE 3

```
CAAGCCCAGAGCCCTGCCATTTCTGTGGGCTCAGTCCCTACTGCTCAGCCCCTT          55
            ─→CD4
                        -20
             M   N   R   G   V   P   F   R   H
CCTCCCTCGGCAAGGCCACAATG AAC CGG GGA GTC CCT TTT AGG CAC         102
        -10                             +10
  L   L   V   L   Q   L   A   L   L   P   A   A   T
  TTG CTT GTG CTG CAA CTG GCG CTC CTC CCA GCA GCC ACT           144
  -1 +1
  Q   G   K   K   V   V   L   G   K   K   G   D   T   V
  CAG GGA AAG AAA GTG GTG CTG GGC AAA AAA GGG GAT ACA GTG       186
                      +20
  E   L   T   C   T   A   S   Q   K   K   S   I   Q   E
  GAA CTG ACC TGT ACA GCT TCC CAG AAG AAG AGC ATA CAA TTC       228
              +30                                 +40
  H   W   K   N   S   N   Q   I   K   I   L   G   N   Q
  CAC TGG AAA AAC TCC AAC CAG ATA AAG ATT CTG GGA AAT CAG       270
                                  +50
  G   S   F   L   T   K   G   P   S   K   L   N   D   R
  GGC TCC TTC TTA ACT AAA GGT CCA TCC AAG CTG AAT GAT CGC       312
```

```
       G   S   F   L   T   K   G   P   S   K   L   N   D   R
      GGC TCC TTC TTA ACT AAA GGT CCA TCC AAG CTG AAT GAT CGC          312
                                +60
       A   D   S   R   R   R   S   L   W   D   Q   G   N   F   P
      GCT GAC TCA AGA AGA AGC CTT TGG GAC CAA GGA AAC TTC CCC          354
         +70                                        +80
       L   I   I   K   N   L   K   I   E   D   Q   D   T   Y
      CTG ATC ATC AAG AAT CTT AAG ATA GAA GAC TCA GAT ACT TAC          396
                                    +90
       I   C   E   V   E   D   Q   K   E   E   V   Q   L   L
      ATC TGT GAA GTG GAG GAC CAG AAG GAG GAG GTG CAA TTG CTA          438
                    +100                                       +110
       V   F   G   L   T   A   N   S   D   T   H   L   L   Q
      GTG TTC GGA TTG ACT GCC AAC TCT GAC ACC CAC CTG CTT CAG          480
                                            +120
       G   Q   S   L   T   L   T   L   E   S   P   P   G   S
      GGG CAG AGC CTG ACC CTG ACC TTG GAG AGC CCC CCT GGT AGT          522
                        +130
       S   P   S   V   Q   C   R   S   P   R   G   K   N   I
      AGC CCC TCA GTG CAA TGT AGG AGT CCA AGG GGT AAA AAC ATA          564
```

```
        +140
          G   G   K   T   L   S   V   S   Q   L   E   L   Q
        CAG GGG GGG AAG ACC CTC TCC GTG TCT CAG CTG GAG CTC CAG    606
                                  +150

D   S   G   T   W   T   C   T   V   L   Q   N   Q   K
        GAT AGT GGC ACC TGG ACA TGC ACT GTC TTG CAG AAC CAG AAG    648
                          +160                          ┌→Hinge
                                                       +180
          K   V   E   F   K   I   D   I   V   V   L   A   F   E
        AAG GTG GAG TTC AAA ATA GAC ATC GTG GTG CTA GCT TTC GAG    690
                  +170

R   K   C   C   V   E   C   P   P   C   P
        CGC AAA TGT TGT GTC GAG TGT CCA CCG TGC CCA GGTAAGCCAGCC    705
                                          +190

CAGGCCTCGCCCCTCCAGCTCAAGGCGGGACAGGTGCCCTAGAGTAGCCTGCATCC    760
                                                      ┌→CH2
                                                       A
        AGGGACAGGCCCCAGCTGGGTGCTGACACGTCCACCTCCATCTCTCTTCCTCAGCA    814

P   P   V   A   G   P   S   V   F   L   F   P   P   K
        CCA CCT GTG GCA GGA CCG TCA GTC TTC CTC TTC CCC CCA AAA    856
                                  +200
```

```
      P   K   D   T   L   M   I   S   R   T   P   E   V   T
    CCC AAG GAC ACC CTC ATG ATC TCC CGG ACC CCT GAG GTC ACG       898
         +210

+220
      C   V   V   V   D   V   S   H   E   D   P   E   V   Q
    TGC GTG GTG GTG GAC GTG AGC CAC GAA GAC CCC GAG GTC CAG       940
                         +230

F   N   W   Y   V   D   G   V   E   V   H   N   A   K
    TTC AAC TGG TAC GTG GAC GGC GTG GAG GTG CAT AAT GCC AAG       982
                 +240

+250                                        +260
      T   K   P   R   E   E   Q   F   N   S   T   F   R   V
    ACA AAG CCA CGG GAG GAG CAG TTC AAC AGC ACG TTC CGT GTG       1024

V   S   V   L   T   V   V   H   Q   D   W   L   N   G
    GTC AGC GTC CTC ACC GTT GTG CAC CAG GAC TGG CTG AAC GGC       1066
                                 +270

+280
      K   E   Y   K   C   K   V   S   N   K   G   L   P   A
    AAG GAG TAC AAG TGC AAG GTC TCC AAC AAA GGC CTC CCA GCC       1108

P   I   E   K   T   I   S   K   T   K
    CCC ATC GAG AAA ACC ATC TCC AAA ACC AAAGGTGGGACCCGCGGGG       1154
    +290
```

```
TATGAGGGCCACATGGACAGAGGCCGGCTCGGCCCACCCTCTGCCCTGGGAGTGA                                    1209
                                      └→CH3
                                    +300
               G   Q   P   R   E   P   Q
CCGCTGTGCCAACCTCTGTCCCTACAGGG CAG CCC CGA GAA CCA CAG                                       1256
       +310                                          +320
 V   Y   T   L   P   P   S   R   E   E   M   T   K   N
GTG TAC ACC CTG CCC CCA TCC CGG GAG GAG ATG ACC AAG AAC                                     1298
                                     +330
 Q   V   S   L   T   C   L   V   K   G   F   Y   P   S
CAG GTC AGC CTG ACC TGC CTG GTC AAA GGC TTC TAC CCC AGC                                     1340
                      +340                                +360
 D   I   A   V   E   W   E   S   N   G   Q   P   E   N
GAC ATC GCC GTG GAG TGG GAG AGC AAT GGG CAG CCG GAG AAC                                     1382
       +350                                       D   G   S
 N   Y   K   T   T   P   P   M   L   D   S   D   G   S
AAC TAC AAG ACC ACA CCT CCC ATG CTG GAC TCC GAC GGC TCC                                     1424
                                +370
 F   F   L   Y   S   K   L   T   V   D   K   S   R   W
TTC TTC CTC TAC AGC AAG CTC ACC GTG GAC AAG AGC AGG TGG                                     1466
```

```
         +380                              +400
   Q   Q   G   N   V   F   S   C   S   V   M   H   E   A
   CAG CAG GGG AAC GTC TTC TCA TGC TCC GTG ATG CAT GAG GCT    1508

+410
   L   H   N   H   Y   T   Q   K   S   L   S   L   S   P
   CTG CAC AAC CAC TAC ACG CAG AAG AGC CTC TCC CTG TCT CCG    1550

G   K   stop
   GGT AAA TGAGTGCCACGGCCAAGCCCCCGCTCCCCAGGCTCTCGGGGTCG       1603

CGTGAGGATGCTTGGCACGTACCCCGTGTACATACTTCCCAGGCACCCAGCATGG    1658

AAATAAAGCACCCAGCGCTGCCCCTGGGCCCCTGCGAGACTGTGATGGTTCTTTCC   1713

GTGGGTCAGGCCGAGTCTGAGGCCTGAGTGGGCATGAGGAGGCAGAGTGGGTC...   1766
```

```
 A   D   S   R   R   S   L   W   D   Q   G   N   F   P
                    +60
GCT GAC TCA AGA AGA AGC CTT TGG GAC CAA GGA AAC TTC CCC    354

L   I   I   K   N   L   K   I   E   D   T   Y
    +70                         +80
CTG ATC ATC AAG AAT CTT AAG ATA GAA GAC ACT TAC            396

I   C   E   V   E   D   Q   K   E   E   V   Q   L   L
                            +90
ATC TGT GAA GTG GAG GAC CAG AAG GAG GAG GTG CAA TTG CTA    438

V   F   G   L   T   A   N   S   D   T   H   L   L   Q
            +100                                    +110
GTG TTC GGA TTG ACT GCC AAC TCT GAC ACC CAC CTG CTT CAG    480

G   Q   S   L   T   L   T   L   E   S   P   P   G   S
                                        +120
GGG CAG AGC CTG ACC CTG ACC TTG GAG AGC CCC CCT GGT AGT    522

S   P   S   V   Q   C   R   S   P   R   G   K   N   I
                        +130
AGC CCC TCA GTG CAA TGT AGG AGT CCA AGG GGT AAA AAC ATA    564
```

```
      +140               +150
   Q   G   G   K   T   L   S   V   S   Q   L   Q
   CAG GGG GGG AAG ACC CTC TCC GTG TCT CAG CTC CAG    606

+160                         →CH1
   D   S   G   T   W   T   C   T   V   L   Q   N   Q   K  +180
   GAT AGT GGC ACC TGG ACA TGC ACT GTC TTG CAG AAC CAG AAG 648
                +170                                      A
   K   V   E   F   K   I   D   I   V   V   L   A   F   A
   AAG GTG GAG TTC AAA ATA GAC ATC GTG GTG CTA GCT TTC GCC 690

+190
   S   T   K   G   P   S   V   F   P   L   A   P   C   S
   TCC ACC AAG GGC CCA TCG GTC TTC CCC CTG GCG CCC TGC TCC 732

+200
   R   S   T   S   E   S   T   A   A   L   G   C   L   V
   AGG AGC ACC TCC GAG AGC ACA GCC GCC CTG GGC TGC CTG GTC 774
      +210                            +220
   K   D   Y   F   P   E   P   V   T   V   S   W   N   S
   AAG GAC TAC TTC CCC GAA CCG GTG ACG GTG TCG TGG AAC TCA 816

+230
   G   A   L   T   S   G   V   H   T   F   P   A   V   L
   GGC GCT CTG ACC AGC GGC GTG CAC ACC TTC CCA GCT GTC CTA 858
```

```
        +240                                    +250
    Q   S   S   G   L   Y   S   L   S   S   V   V   T   V
    CAG TCC TCA GGA CTC TAC TCC CTC AGC AGC GTG GTG ACC GTG    900

+260
    P   S   S   N   F   G   T   Q   T   Y   T   C   N   V
    CCC TCC AGC AAC TTC GGC ACC CAG ACC TAC ACC TGC AAC GTA    942

+270
    D   H   K   P   S   N   T   K   V   D   K   T   V
    GAT CAC AAG CCC AGC AAC ACC AAG GTG GAC AAG ACA GTTGGTG    985

AGAGGCCAGCTCAGGGAGGTGTCTGCTGAAGCCAGGCTCAGCCCTCCTG          1040

CCTGGACGCACCCCGGCTGTGCAGCCCCAGGGCAGCAAGGCAGGCCCCAT         1095

CTGTCTCCTCACCCGGAGCCTCTGCCCGCCCCACTCATGCTCAGGGAGAGGGTC     1150

TTCTGCTTTTTCCACCAGGCTCCAGGCAGCACAGGCTGGGTGCCCCTACCCCA      1205

GGCCCTTCACACAGGGGCAGGTGCTTGGCTCAGACCTGCCAAAAGCCATATCC      1260
```

```
GGGAGGACCCTGCCCCTGACCTAAGCCGACCCCAAAGGCCAAACTGTCCACTCCC            1315

TCAGCTCGGACACCTTCTCTCCTCCCAGATCCGAGTAACTCCCAATCTTCTCTCT            1370
    └→Hinge
       +280
     E   R   K   C   C   V   E   C   P   P   C   P
    GCAGAG CGC AAA TGT TGT GTC GAG TGC CCA CCG TGC CCAGGTAAG         1415

CCAGCCCAGGCCTCGCCCTCCAGCTCAAGGGGGACAGGTGCCCTAGAGTAGCCT             1470

GCATCCAGGGACACAGGCCCCAGCTGGGTGCTGACACGTCCACCTCCATCTCTTCCT          1525
    └→CH2
       +290                              +300
     A   P   P   V   A   G   P   S   V   F   L   F   P   P
    CAGCA CCA CCT GTG GCA GGA CCG TCA GTC TTC CTC TTC CCC CCA        1569

+310
     K   P   K   D   T   L   M   I   S   R   T   P   E   V
    AAA CCC AAG GAC ACC CTC ATG ATC TCC CGG ACC CCT GAG GTC          1611

+320                              +330
     T   C   V   V   V   D   V   S   H   E   D   P   E   V
    ACG TGC GTG GTG GTG GAC GTG AGC CAC GAA GAC CCC GAG GTC          1653
```

```
  Q   F   N   W   Y   V   D   G   V   E   V   H   N   A
CAG TTC AAC TGG TAC GTG GAC GGC GTG GAG GTG CAT AAT GCC    1695
                          +340

K   T   K   P   R   E   E   Q   F   N   S   T   F   R
AAG ACA AAG CCA CGG GAG GAG CAG TTC AAC AGC ACG TTC CGT    1737
                  +350

+360
  V   V   S   V   L   T   V   V   H   Q   D   W   L   N
GTG GTC AGC GTC CTC ACC GTT GTG CAC CAG GAC TGG CTG AAC    1779
                                          +370

G   K   E   Y   K   C   K   V   S   N   K   G   L   P
GGC AAG GAG TAC AAG TGC AAG GTC TCC AAC AAA GGC CTC CCA    1821
                                  +380

+390
  A   P   I   E   K   T   I   S   K   T   K
GCC CCC ATC GAG AAA ACC ATC TCC AAA ACC AAAGGTGGGACCCGC    1866

GGGGTATGAGGGCCACATGGACAGAGGCCGGCTCGGCCCACCCTCTGCCCTGGGA    1921
                                   ┌─CH3
                                   │ +400
                                   └ G   Q   P   R   E   P   Q
GTGACCGCTGTGCCAACCTCTGTCCCTACAGGG CAG CCC CGA GAA CCA CAG    1972
```

```
        V   Y   T   L   P   P   S   R   E   E   M   T   K   N
        GTG TAC ACC CTG CCC CCA TCC CGG GAG GAG ATG ACC AAG AAC     2014
            +410                                +430

Q   V   S   L   T   C   L   V   K   G   F   Y   P   S
        CAG GTC AGC CTG ACC TGC CTG GTC AAA GGC TTC TAC CCC AGC     2056
        +420

D   I   A   V   E   W   E   S   N   G   Q   P   E   N
        GAC ATC GCC GTG GAG TGG GAG AGC AAT GGG CAG CCG GAG AAC     2098
                            +440                        +460

N   Y   K   T   T   P   P   M   L   D   S   D   G   S
        AAC TAC AAG ACC ACA CCT CCC ATG CTG GAC TCC GAC GGC TCC     2140
            +450                            +470

F   F   L   Y   S   K   L   T   V   D   K   S   R   W
        TTC TTC CTC TAC AGC AAG CTC ACC GTG GAC AAG AGC AGG TGG     2182
                                +480

Q   Q   G   N   V   F   S   C   S   V   M   H   E   A
        CAG CAG GGG AAC GTC TTC TCA TGC TCC GTG ATG CAT GAG GCT     2224
                                                    +500

L   H   N   H   Y   T   Q   K   S   L   S   L   S   P
        CTG CAC AAC CAC TAC ACG CAG AAG AGC CTC TCC CTG TCT CCG     2266
        +490
```

```
  G   K   stop
GGT AAA TGAGTGCCACGGCCGGCAAGCCCCCGCTCCCCAGGCTCTCGGGGTCG      2319

CGTGAGGATGCTTGGCACGTACCCCGTGTACATACTTCCCAGGCACCCAGCATGG      2374

AAATAAAGCACCCCAGCGCTGCCCCTGGGCCCCTGCGAGACTGTGATGGTTCTTTCC   2429

GTGGGTCAGGCCCGAGTCTGAGGCCTGAGTGTGGCATGAGGAGGCAGAGTGGGTC...  2482
```

FIGURE 5

```
CAAGCCCAGAGCCCTGCCATTTCTGTGGGCTCAGGTCCCTACTGCTCAGCCCCTT                    55
                                              -20
                     →CD4       M  N  R  G  V  P  F  R  H
CCTCCCTCGGCAAGGCCACAATG AAC CGG GGA GTC CCT TTT AGG CAC                   102
                              -10
    L  L  L  V  L  Q   L  A  L  L  P  A  A  T
    TTG CTT CTG GTG CTG CAA CTG GCG CTC CTC CCA GCA GCC ACT               144
  -1 +1                                              +10
    Q  G  K  K  V  V  L  G  K  K  G  D  T  V
    CAG GGA AAG AAA GTG GTG CTG GGC AAA AAA GGG GAT ACA GTG               186
                                  +20
    E  L  T  C  T  A  S  Q  K  K  S  I  Q  F
    GAA CTG ACC TGT ACA GCT TCC CAG AAG AAG AGC ATA CAA TTC               228
                +30                                       +40
    H  W  K  N  S  N  Q  I  K  I  L  G  N  Q
    CAC TGG AAA AAC TCC AAC CAG ATA AAG ATT CTG GGA AAT CAG               270
                              +50
    G  S  F  L  T  K  G  P  S  K  L  N  D  R
    GGC TCC TTC TTA ACT AAA GGT CCA TCC AAG CTG AAT GAT CGC               312
```

```
      A   D   S   R   R   S   L   W   D   Q   G   N   F   P
      GCT GAC TCA AGA AGA AGC CTT TGG GAC CAA GGA AAC TTC CCC    354
                          +60
      L   I   I   K   N   L   K   I   E   D   S   D   T   Y
      CTG ATC ATC AAG AAT CTT AAG ATA GAA GAC TCA GAT ACT TAC    396
         +70                              +80
      I   C   E   V   E   D   Q   K   E   E   V   Q   L   L
      ATC TGT GAA GTG GAG GAC CAG AAG GAG GAG GTG CAA TTG CTA    438
                                  +90
      V   F   G   L   T   A   N   S   D   T   H   L   L   Q
      GTG TTC GGA TTG ACT GCC AAC TCT GAC ACC CAC CTG CTT CAG    480
                     +100                                 +110
      G   Q   S   L   T   L   T   L   E   S   P   P   G   S
      GGG CAG AGC CTG ACC CTG ACC TTG GAG AGC CCC CCT GGT AGT    522
                                          +120
      S   P   S   V   Q   C   R   S   P   R   G   K   N   I
      AGC CCC TCA GTG CAA TGT AGG AGT CCA AGG GGT AAA AAC ATA    564
                          +130
```

```
        +140                                                              +150
         Q    G    G    K    T    L    S    V    S    Q    L    E    L    Q
        CAG  GGG  GGG  AAG  ACC  CTC  TCC  GTG  TCT  CAG  CTG  GAG  CTC  CAG         606

+160                                              Ckappa
         D    S    G    T    W    T    C    T    V    L    Q    N    Q    K
        GAT  AGT  GGC  ACC  TGG  ACA  TGC  ACT  GTC  TTG  CAG  AAC  CAG  AAG         648
                        +170                                            +180
         K    V    E    F    K    I    D    I    V    V    L    A    F    T
        AAG  GTG  GAG  TTC  AAA  ATA  GAC  ATC  GTG  GTG  CTA  GCT  TTC  ACT         690

+190
         V    A    A    P    S    V    F    I    F    P    P    S    D    E
        GTG  GCT  GCA  CCA  TCT  GTC  TTC  ATC  TTC  CCG  CCA  TCT  GAT  GAG         732

+200                          +220
         Q    L    K    S    G    T    A    S    V    V    C    L    L    N
        CAG  TTG  AAA  TCT  GGA  ACT  GCC  TCT  GTT  GTG  TGC  CTG  CTG  AAT         774
             +210
         N    F    Y    P    R    E    A    K    V    Q    W    K    V    D
        AAC  TTC  TAT  CCC  AGA  GAG  GCC  AAA  GTA  CAG  TGG  AAG  GTG  GAT         716
                                             +230
         N    A    L    Q    S    G    N    S    Q    E    S    V    T    E
        AAC  GCC  CTC  CAA  TCG  GGT  AAC  TCC  CAG  GAG  AGT  GTC  ACA  GAG         758
```

```
          +240                    +250
  Q   D   S   K   D   S   T   Y   S   L   S   T   L
CAG GAC AGC AAG GAC AGC ACC TAC AGC CTC AGC ACC CTG      900

+260
  T   L   S   K   A   D   Y   E   K   H   K   V   Y   A
ACG CTG AGC AAA GCA GAC TAC GAG AAA CAC AAA GTC TAC GCC  942

+270
  C   E   V   T   H   Q   G   L   S   S   P   V   T   K
TGC GAA GTC ACC CAT CAG GGC CTG AGC TCG CCC GTC ACA AAG  984

+280
  S   F   N   R   G   E   C  stop
AGC TTC AAC AGG GGA GAG TGT TAG AGGGAGAAGTGCCCCACCTGCTC 1032

CTCAGTTCCAGCCTGACCCCCTCCCATCCCTTGGCCTCTGACCCTTTTCCACAGG 1088

GGACCTACCCCTATTGCGGTCCTCCAAGCTCATCTTTCACCTCACCCCCCCTCC  1144

TCCTT
```

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 13 amino acids
      (B) TYPE: amino acid
      (C) STRANDEDNESS: unknown
      (D) TOPOLOGY: unknown (ii) MOLECULE TYPE: peptide (vi) ORIGINAL SOURCE:
      (A) ORGANISM: homo sapien
      (G) CELL TYPE: lymphocyte (xi) SEQUENCE DESCRIPTION: SEQ ID NO:1:

Phe Glu Arg Lys Cys Cys Val Gln Cys Pro Pro Cys Asp
1           5                 10

(2) INFORMATION FOR SEQ ID NO:2:

(i) SEQUENCE CHARACTERISTICS:
      (A) LENGTH: 1796 base pairs
      (B) TYPE: nucleic acid
      (C) STRANDEDNESS: double
      (D) TOPOLOGY: unknown (ii) MOLECULE TYPE: cDNA (vi) ORIGINAL SOURCE:
    (A) ORGANISM: Homo sapiens
    (G) CELL TYPE: Lymphocyte (xi) SEQUENCE DESCRIPTION: SEQ ID NO:2:

```
CAAGCCCAGA GCCCTGCCAT TTCTGTGGGC TCAGGTCCCT ACTGCTCAGC CCCTTCCTCC      60
CTCGGCAAGG CCACAATGAA CCGGGGAGTC CCTTTTAGGC ACTTGCTTCT GGTGCTGCAA     120
CTGGCGCTCC TCCCAGCAGC CACTCAGGGA AGAAAGTGG  TGCTGGGCAA AAAAGGGGAT     180
ACAGTGGAAC TGACCTGTAC AGCTTCCCAG AAGAAGAGCA TACAATTCCA CTGGAAAAAC     240
TCCAACCAGA TAAAGATTCT GGGAAATCAG GGCTCCTTCT TAACTAAAGG TCCATCCAAG     300
CTGAATGATC GCGCTGACTC AAGAAGAAGC CTTTGGGACC AAGGAAACTT CCCCCTGATC     360
ATCAAGAATC TTAAGATAGA AGACTCAGAT ACTTACATCT GTGAAGTGGA GGACCAGAAG     420
GAGGAGGTGC AATTGCTAGT GTTCGGATTG ACTGCCAACT CTGACACCCA CCTGCTTCAG     480
GGGCAGAGCC TGACCCTGAC CTTGGAGAGC CCCCCTGGTA GTAGCCCCTC AGTGCAATGT     540
AGGAGTCCAA GGGGTAAAAA CATACAGGGG GGGAAGACCC TCTCCGTGTC TCAGCTGGAG     600
CTCCAGGATA GTGGCACCTG GACATGCACT GTCTTGCAGA ACCAGAAGAA GGTGGAGTTC     660
AAAATAGACA TCGTGGTGCT AGCTTTCGAG CGCAAATGTT GTGTCGAGTG CCCACCGTGC     720
CCAGGTAAGC CAGCCCAGGC CTCGCCCTCC AGCTCAAGGC GGGACAGGTG CCCTAGAGTA     780
GCCTGCATCC AGGGACAGGC CCCAGCTGGG TGCTGACACG TCCACCTCCA TCTCTTCCTC     840
AGCACCACCT GTGGCAGGAC CGTCAGTCTT CCTCTTCCCC CCAAAACCCA AGGACACCCT     900
CATGATCTCC CGGACCCCTG AGGTCACGTG CGTGGTGGTG GACGTGAGCC ACGAAGACCC     960
CGAGGTCCAG TTCAACTGGT ACGTGGACGG CGTGGAGGTG CATAATGCCA AGACAAAGCC    1020
ACGGGAGGAG CAGTTCAACA GCACGTTCCG TGTGGTCAGC GTCCTCACCG TTGTGCACCA    1080
GGACTGGCTG AACGGCAAGG AGTACAAGTG CAAGGTCTCC AACAAAGGCC TCCCAGCCCC    1140
CATCGAGAAA ACCATCTCCA AAACCAAAGG TGGGACCCGC GGGGTATGAG GGCCACATGG    1200
ACAGAGGCCG GCTCGGCCCA CCCTCTGCCC TGGGAGTGAC CGCTGTGCCA ACCTCTGTCC    1260
CTACAGGGCA GCCCCGAGAA CCACAGGTGT ACACCCTGCC CCCATCCCGG GAGGAGATGA    1320
CCAAGAACCA GGTCAGCCTG ACCTGCCTGG TCAAAGGCTT CTACCCCAGC GACATCGCCG    1380
TGGAGTGGGA GAGCAATGGG CAGCCGGAGA ACAACTACAA GACCACACCT CCCATGCTGG    1440
ACTCCGACGG CTCCTTCTTC CTCTACAGCA AGCTCACCGT GGACAAGAGC AGGTGGCAGC    1500
AGGGGAACTG CTTCTCATGC TCCGTGATGC ATGAGGCTCT GCACAACCAC TACACGCAGA    1560
AGAGCCTCTC CCTGTCTCCG GGTAAATGAG TGCCACGGCC GGCAAGCCCC CGCTCCCCAG    1620
GCTCTCGGGG TCGCGTGAGG ATGCTTGGCA CGTACCCCGT GTACATACTT CCCAGGCACC    1680
CAGCATGGAA ATAAAGCACC CAGCGCTGCC CTGGGCCCCT GCGAGACTGT GATGGTTCTT    1740
TCCGTGGGTC AGGCCGAGTC TGAGGCCTGA GTGGCATGAG GGAGGCAGAG TGGGTC         1796
```

(2) INFORMATION FOR SEQ ID NO:3:

(i) SEQUENCE CHARACTERISTICS:
       (A) LENGTH: 432 amino acids
       (B) TYPE: amino acid
       (C) STRANDEDNESS: unknown
       (D) TOPOLOGY: unknown (ii) MOLECULE TYPE: protein (vi) ORIGINAL SOURCE:

-continued (A) ORGANISM: homo sapien
(G) CELL TYPE: lymphocyte (xi) SEQUENCE DESCRIPTION: SEQ ID NO:3:

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Glu Arg Lys Cys
                195                 200                 205

Cys Val Glu Cys Pro Pro Cys Pro Ala Pro Pro Val Ala Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Gln Phe Asn Trp Tyr Val Asp Gly Val Glu Val His Asn Ala
            260                 265                 270

Lys Thr Lys Pro Arg Glu Glu Gln Phe Asn Ser Thr Phe Arg Val Val
        275                 280                 285

Ser Val Leu Thr Val Val His Gln Asp Trp Leu Asn Gly Lys Glu Tyr
290                 295                 300

Lys Cys Lys Val Ser Asn Lys Gly Leu Pro Ala Pro Ile Glu Lys Thr
305                 310                 315                 320

Ile Ser Lys Thr Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
                355                 360                 365

Asn Gly Gln Pro Glu Asn Asn Tyr Lys Thr Thr Pro Pro Met Leu Asp
370                 375                 380

Ser Asp Gly Ser Phe Phe Leu Tyr Ser Lys Leu Thr Val Asp Lys Ser
385                 390                 395                 400
```

-continued

```
Arg Trp Gln Gln Gly Asn Val Phe Ser Cys Ser Val Met His Glu Ala
              405                 410                 415

Leu His Asn His Tyr Thr Gln Lys Ser Leu Ser Leu Ser Pro Gly Lys
              420                 425                 430

(2) INFORMATION FOR SEQ ID NO:4:

(i) SEQUENCE CHARACTERISTICS:
        (A) LENGTH: 2482 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:4:

CAAGCCCAGA GCCCTGCCAT TTCTGTGGGC TCAGGTCCCT ACTGCTCAGC CCCTTCCTCC      60

CTCGGCAAGG CCACAATGAA CCGGGGAGTC CCTTTTAGGC ACTTGCTTCT GGTGCTGCAA     120

CTGGCGCTCC TCCCAGCAGC CACTCAGGGA AGAAAGTGG TGCTGGGCAA AAAAGGGGAT     180

ACAGTGGAAC TGACCTGTAC AGCTTCCCAG AAGAAGAGCA TACAATTCCA CTGGAAAAAC    240

TCCAACCAGA TAAAGATTCT GGGAAATCAG GGCTCCTTCT TAACTAAAGG TCCATCCAAG    300

CTGAATGATC GCGCTGACTC AAGAAGAAGC CTTTGGGACC AAGGAAACTT CCCCCTGATC    360

ATCAAGAATC TTAAGATAGA AGACTCAGAT ACTTACATCT GTGAAGTGGA GGACCAGAAG    420

GAGGAGGTGC AATTGCTAGT GTTCGGATTG ACTGCCAACT CTGACACCCA CCTGCTTCAG    480

GGGCAGAGCC TGACCCTGAC CTTGGAGAGC CCCCCTGGTA GTAGCCCCTC AGTGCAATGT    540

AGGAGTCCAA GGGGTAAAAA CATACAGGGG GGGAAGACCC TCTCCGTGTC TCAGCTGGAG    600

CTCCAGGATA GTGGCACCTG GACATGCACT GTCTTGCAGA ACCAGAAGAA GGTGGAGTTC    660

AAAATAGACA TCGTGGTGCT AGCTTTCGCC TCCACCAAGG GCCCATCGGT CTTCCCCCTG    720

GCGCCCTGCT CCAGGAGCAC CTCCGAGAGC ACAGCCGCCC TGGGCTGCCT GGTCAAGGAC    780

TACTTCCCCG AACCGGTGAC GGTGTCGTGG AACTCAGGCG CTCTGACCAG CGGCGTGCAC    840

ACCTTCCCAG CTGTCCTACA GTCCTCAGGA CTCTACTCCC TCAGCAGCGT GGTGACCGTG    900

CCCTCCAGCA ACTTCGGCAC CCAGACCTAC ACCTGCAACG TAGATCACAA GCCCAGCAAC    960

ACCAAGGTGG ACAAGACAGT TGGTGAGAGG CCAGCTCAGG GAGGGAGGGT GTCTGCTGGA   1020

AGCCAGGCTC AGCCCTCCTG CCTGGACGCA CCCCGGCTGT GCAGCCCCAG CCCAGGGCAG   1080

CAAGGCAGGC CCCATCTGTC TCCTCACCCG GAGGCCTCTG CCCGCCCCAC TCATGCTCAG   1140

GGAGAGGGTC TTCTGGCTTT TTCCACCAGG CTCCAGGCAG GCACAGGCTG GGTGCCCCTA   1200

CCCCAGGCCC TTCACACACA GGGGCAGGTG CTTGGCTCAG ACCTGCCAAA AGCCATATCC   1260

GGGAGGACCC TGCCCCTGAC CTAAGCCGAC CCCAAAGGCC AAACTGTCCA CTCCCTCAGC   1320

TCGGACACCT TCTCTCCTCC CAGATCCGAG TAACTCCCAA TCTTCTCTCT GCAGAGCGCA   1380

AATGTTGTGT CGAGTGCCCA CCGTGCCCAG GTAAGCCAGC CCAGGCCTCG CCCTCCAGCT   1440

CAAGGCGGGA CAGGTGCCCT AGAGTAGCCT GCATCCAGGG ACAGGCCCCA GCTGGGTGCT   1500

GACACGTCCA CCTCCATCTC TTCCTCAGCA CCACCTGTGG CAGGACCGTC AGTCTTCCTC   1560

TTCCCCCCAA AACCCAAGGA CACCCTCATG ATCTCCCGGA CCCCTGAGGT CACGTGCGTG   1620

GTGGTGGACG TGAGCCACGA AGACCCCGAG GTCCAGTTCA ACTGGTACGT GGACGGCGTG   1680
```

-continued

```
GAGGTGCATA ATGCCAAGAC AAAGCCACGG GAGGAGCAGT TCAACAGCAC GTTCCGTGTG    1740

GTCAGCGTCC TCACCGTTGT GCACCAGGAC TGGCTGAACG GCAAGGAGTA CAAGTGCAAG    1800

GTCTCCAACA AAGGCCTCCC AGCCCCCATC GAGAAAACCA TCTCCAAAAC CAAAGGTGGG    1860

ACCCGCGGGG TATGAGGGCC ACATGGACAG AGGCCGGCTC GGCCCACCCT CTGCCCTGGG    1920

AGTGACCGCT GTGCCAACCT CTGTCCCTAC AGGGCAGCCC CGAGAACCAC AGGTGTACAC    1980

CCTGCCCCCA TCCCGGGAGG AGATGACCAA GAACCAGGTC AGCCTGACCT GCCTGGTCAA    2040

AGGCTTCTAC CCCAGCGACA TCGCCGTGGA GTGGGAGAGC AATGGGCAGC CGGAGAACAA    2100

CTACAAGACC ACACCTCCCA TGCTGGACTC CGACGGCTCC TTCTTCCTCT ACAGCAAGCT    2160

CACCGTGGAC AAGAGCAGGT GGCAGCAGGG GAACGTCTTC TCATGCTCCG TGATGCATGA    2220

GGCTCTGCAC AACCACTACA CGCAGAAGAG CCTCTCCCTG TCTCCGGGTA AATGAGTGCC    2280

ACGGCCGGCA AGCCCCCGCT CCCCAGGCTC TCGGGGTCGC GTGAGGATGC TTGGCACGTA    2340

CCCCGTGTAC ATACTTCCCA GGCACCCAGC ATGGAAATAA AGCACCCAGC GCTGCCCTGG    2400

GCCCCTGCGA GACTGTGATG GTTCTTTCCG TGGGTCAGGC CGAGTCTGAG GCCTGAGTGG    2460

CATGAGGGAG GCAGAGTGGG TC                                             2482
```

(2) INFORMATION FOR SEQ ID NO:5:

(i) SEQUENCE CHARACTERISTICS:
        (A) LENGTH: 530 amino acids
        (B) TYPE: amino acid
        (C) STRANDEDNESS: unknown
        (D) TOPOLOGY: unknown (ii) MOLECULE TYPE: cDNA (vi) ORIGINAL SOURCE:
        (A) ORGANISM: homo sapien
        (G) CELL TYPE: lymphocyte (xi) SEQUENCE DESCRIPTION: SEQ ID NO:5:

```
Met Asn Arg Gly Val Pro Phe Arg His Leu Leu Leu Val Leu Gln Leu
1               5                  10                  15

Ala Leu Leu Pro Ala Ala Thr Gln Gly Lys Lys Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175
```

-continued

```
Gln Asp Ser Gly Thr Trp Thr Cys Thr Val Leu Gln Asn Gln Lys Lys
            180                 185                 190

Val Glu Phe Lys Ile Asp Ile Val Leu Ala Phe Ala Ser Thr Lys
            195                 200             205

Gly Pro Ser Val Phe Pro Leu Ala Pro Cys Ser Arg Ser Thr Ser Glu
210                 215                 220

Ser Thr Ala Ala Leu Gly Cys Leu Val Lys Asp Tyr Phe Pro Glu Pro
225                 230                 235                 240

Val Thr Val Ser Trp Asn Ser Gly Ala Leu Thr Ser Gly Val His Thr
                245                 250                 255

Phe Pro Ala Val Leu Gln Ser Ser Gly Leu Tyr Ser Leu Ser Ser Val
                260                 265                 270

Val Thr Val Pro Ser Ser Asn Phe Gly Thr Gln Thr Tyr Thr Cys Asn
            275                 280                 285

Val Asp His Lys Pro Ser Asn Thr Lys Val Asp Lys Thr Val Glu Arg
290                 295                 300

Lys Cys Cys Val Glu Cys Pro Pro Cys Pro Ala Pro Pro Val Ala Gly
305                 310                 315                 320

Pro Ser Val Phe Leu Phe Pro Pro Lys Pro Lys Asp Thr Leu Met Ile
                325                 330                 335

Ser Arg Thr Pro Glu Val Thr Cys Val Val Val Asp Val Ser His Glu
                340                 345                 350

Asp Pro Glu Val Gln Phe Asn Trp Tyr Val Asp Gly Val Glu Val His
            355                 360                 365

Asn Ala Lys Thr Lys Pro Arg Glu Glu Gln Phe Asn Ser Thr Phe Arg
370                 375                 380

Val Val Ser Val Leu Thr Val Val His Gln Asp Trp Leu Asn Gly Lys
385                 390                 395                 400

Glu Tyr Lys Cys Lys Val Ser Asn Lys Gly Leu Pro Ala Pro Ile Glu
                405                 410                 415

Lys Thr Ile Ser Lys Thr Lys Gly Gln Pro Arg Glu Pro Gln Val Tyr
                420                 425                 430

Thr Leu Pro Pro Ser Arg Glu Glu Met Thr Lys Asn Gln Val Ser Leu
            435                 440                 445

Thr Cys Leu Val Lys Gly Phe Tyr Pro Ser Asp Ile Ala Val Glu Trp
450                 455                 460

Glu Ser Asn Gly Gln Pro Glu Asn Asn Tyr Lys Thr Thr Pro Pro Met
465                 470                 475                 480

Leu Asp Ser Asp Gly Ser Phe Phe Leu Tyr Ser Lys Leu Thr Val Asp
                485                 490                 495

Lys Ser Arg Trp Gln Gln Gly Asn Val Phe Ser Cys Ser Val Met His
            500                 505                 510

Glu Ala Leu His Asn His Tyr Thr Gln Lys Ser Leu Ser Leu Ser Pro
            515                 520                 525

Gly Lys
530
```

(2) INFORMATION FOR SEQ ID NO:6:

(i) SEQUENCE CHARACTERISTICS:
        (A) LENGTH: 1149 base pairs
        (B) TYPE: nucleic acid
        (C) STRANDEDNESS: double
        (D) TOPOLOGY: unknown (ii) MOLECULE TYPE: cDNA (vi) ORIGINAL SOURCE:
    (A) ORGANISM: homo sapien
    (G) CELL TYPE: lymphocyte (xi) SEQUENCE DESCRIPTION: SEQ ID NO:6:

```
CAAGCCCAGA GCCCTGCCAT TTCTGTGGGC TCAGGTCCCT ACTGCTCAGC CCCTTCCTCC      60
CTCGGCAAGG CCACAATGAA CCGGGGAGTC CCTTTTAGGC ACTTGCTTCT GGTGCTGCAA     120
CTGGCGCTCC TCCCAGCAGC CACTCAGGGA AGAAAGTGG TGCTGGGCAA AAAAGGGGAT     180
ACAGTGGAAC TGACCTGTAC AGCTTCCCAG AAGAAGAGCA TACAATTCCA CTGGAAAAAC     240
TCCAACCAGA TAAAGATTCT GGGAAATCAG GGCTCCTTCT TAACTAAAGG TCCATCCAAG     300
CTGAATGATC GCGCTGACTC AAGAAGAAGC CTTTGGGACC AAGGAAACTT CCCCCTGATC     360
ATCAAGAATC TTAAGATAGA AGACTCAGAT ACTTACATCT GTGAAGTGGA GGACCAGAAG     420
GAGGAGGTGC AATTGCTAGT GTTCGGATTG ACTGCCAACT CTGACACCCA CCTGCTTCAG     480
GGGCAGAGCC TGACCCTGAC CTTGGAGAGC CCCCCTGGTA GTAGCCCCTC AGTGCAATGT     540
AGGAGTCCAA GGGGTAAAAA CATACAGGGG GGGAAGACCC TCTCCGTGTC TCAGCTGGAG     600
CTCCAGGATA GTGGCACCTG GACATGCACT GTCTTGCAGA ACCAGAAGAA GGTGGAGTTC     660
AAAATAGACA TCGTGGTGCT AGCTTTCACT GTGGCTGCAC CATCTGTCTT CATCTTCCCG     720
CCATCTGATG AGCAGTTGAA ATCTGGAACT GCCTCTGTTG TGTGCCTGCT GAATAACTTC     780
TATCCCAGAG AGGCCAAAGT ACAGTGGAAG GTGGATAACG CCCTCCAATC GGGTAACTCC     840
CAGGAGAGTG TCACAGAGCA GGACAGCAAG GACAGCACCT ACAGCCTCAG CAGCACCCTG     900
ACGCTGAGCA AAGCAGACTA CGAGAAACAC AAAGTCTACG CCTGCGAAGT CACCCATCAG     960
GGCCTGAGCT CGCCCGTCAC AAAGAGCTTC AACAGGGGAG AGTGTTAGAG GGAGAAGTGC    1020
CCCCACCTGC TCCTCAGTTC CAGCCTGACC CCCTCCCATC CTTTGGCCTC TGACCCTTTT    1080
TCCACAGGGG ACCTACCCCT ATTGCGGTCC TCCAAGCTCA TCTTTCACCT CACCCCCCTC    1140
CTCCTCCTTT                                                           1149
```

(2) INFORMATION FOR SEQ ID NO:7:

(i) SEQUENCE CHARACTERISTICS:
        (A) LENGTH: 310 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: homo sapien
        (G) CELL TYPE: lymphocyte (xi) SEQUENCE DESCRIPTION: SEQ ID NO:7:

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80
```

```
Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Thr Val Ala Ala
                195                 200                 205

Pro Ser Val Phe Ile Phe Pro Pro Ser Asp Glu Gln Leu Lys Ser Gly
    210                 215                 220

Thr Ala Ser Val Val Cys Leu Leu Asn Asn Phe Tyr Pro Arg Glu Ala
225                 230                 235                 240

Lys Val Gln Trp Lys Val Asp Asn Ala Leu Gln Ser Gly Asn Ser Gln
                245                 250                 255

Glu Ser Val Thr Glu Gln Asp Ser Lys Asp Ser Thr Tyr Ser Leu Ser
            260                 265                 270

Ser Thr Leu Thr Leu Ser Lys Ala Asp Tyr Glu Lys His Lys Val Tyr
    275                 280                 285

Ala Cys Glu Val Thr His Gln Gly Leu Ser Ser Pro Val Thr Lys Ser
    290                 295                 300

Phe Asn Arg Gly Glu Cys
305                 310

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: unknown (ii) MOLECULE TYPE: synthetic DNA (vi) ORIGINAL SOURCE:
        (A) ORGANISM:
        (G) CELL TYPE:

(xi) SEQUENCE DESCRIPTION: SEQ ID NO:8:

GACACAACAT TTGCGCTCGA AAGCTAGCAC CACG                                      34

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: synthetic DNA (vi) ORIGINAL SOURCE:
        (A) ORGANISM:
        (G) CELL TYPE:
```

```
        (xi) SEQUENCE DESCRIPTION: SEQ ID NO:9:

GGGCCCTTGG TGGAGGCGAA AGCTAGCACC ACG                                     33

(2) INFORMATION FOR SEQ ID NO:10:

(i) SEQUENCE CHARACTERISTICS:
         (A) LENGTH: 33 base pairs
         (B) TYPE: nucleic acid
         (C) STRANDEDNESS: single
         (D) TOPOLOGY: unknown (ii) MOLECULE TYPE: synthetic DNA (vi) ORIGINAL SOURCE:
         (A) ORGANISM:
         (G) CELL TYPE:

(xi) SEQUENCE DESCRIPTION: SEQ ID NO:10:

GATGGTGCAG CCACAGTGAA AGCTAGCACC ACG                                     33
```

US 7,070,991 B2

CELLS EXPRESSING A CD4-IGG2 CHIMERIC HETEROTETRAMER

This application is a continuation of U.S. Ser. No. 07/960,440, filed Dec. 8, 1992, now abandoned, which is a 371 national stage application of PCT International Application No. PCT/US92/01143, filed Feb. 10, 1992, which is a continuation-in-part of U.S. Ser. No. 07/653,684, filed Feb. 8, 1991, now abandoned.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

The life cycle of animal viruses is characterized by a series of events that are required for the productive infection of the host cell. The initial step in the replicative cycle is the attachment of the virus to the cell surface which is mediated by the specific interaction of the viral attachment protein (VAP) to receptors on the surface of the target cell. The pattern of expression of these receptors is largely responsible for the host range and tropic properties of viruses. The interaction of the VAP with cellular receptors therefore plays a critical role in infection and pathogenesis of viral diseases and represents an important area to target the development of anti-viral therapeutics.

Cellular receptors may be comprised of all the components of membranes, including proteins, carbohydrates, and lipids. Identification of the molecules mediating the attachment of viruses to the target cell surface has been made in a few instances. The most extensively characterized viral receptor protein is CD4 (T4) (1). CD4 is a nonpolymorphic cell surface glycoprotein that is expressed primarily on the surface of helper T lymphocytes and cells of the monocyte/macrophage lineage. CD4 associates with major histocompatibility complex (MHC) class II molecules on the surface of antigen-presenting cells to mediate efficient cellular immune response interactions. In man, CD4 is also the target of interaction with the human immunodeficiency virus (HIV).

HIV infects primarily helper T lymphocytes and monocytes/macrophages, cells that express surface CD4, leading to a gradual loss of immune function which results in the development of the human acquired immune deficiency syndrome (AIDS). The initial phase of the HIV replicative cycle involves the high affinity interaction between the HIV exterior envelope glycoprotein gp120 and surface CD4 (Kd approximately $4\times10^{-9}$ M) (2). Several lines of evidence demonstrate the requirement of this interaction for viral infectivity. In vitro, the introduction of a functional cDNA encoding CD4 into human cells which do not express CD4 is sufficient to render otherwise resistant cells susceptible to HIV infection (3). In vivo, viral infection appears to be restricted to cells expressing CD4. Following the binding of HIV gp120 to cell surface CD4, viral and target cell membranes fuse, resulting in the introduction of the viral capsid into the target cell cytoplasm.

Characterization of the interaction between HIV gp120 and CD4 has been facilitated by the isolation of cDNA clones encoding both molecules (4, 5). CD4 is a nonpolymorphic, lineage-restricted cell surface glycoprotein that is a member of the immunoglobulin gene superfamily. High-level expression of both full-length CD4 and truncated, soluble versions of CD4 (sCD4) have been described in stable expression systems. The availability of large quantities of purified sCD4 has permitted a detailed understanding of the structure of this complex glycoprotein. Mature CD4 has a relative molecular mass (Mr) of 55 kilodaltons and consists of an amino-terminal 372 amino acid extracellular domain containing four tandem immunoglobulin-like regions denoted V1–V4, followed by a 23 amino acid transmembrane domain and a 38 amino acid cytoplasmic segment. The amino-terminal immunoglobulin-like domain V1 bears 32% homology with kappa light chain variable domains. Three of the four immunoglobulin-like domains contain a disulphide bond (V1, V2 and V4), and both N-linked glycosylation sites in the carboxy-terminal portion of the molecule are utilized (4, 6).

Experiments using truncated sCD4 proteins demonstrate that the determinants of high-affinity binding to HIV gp120 lie within the amino-terminal immunoglobulin-like domain V1 (7–9). Mutational analysis of V1 has defined a discrete gp120 binding site (residues 38–52 of the mature CD4 protein) that comprises a region structurally homologous to the second complementarity-determining region (CDR2) of immunoglobulins (9). The production of large quantities of V1V2 has permitted a structural analysis of the two amino-terminal immunoglobulin-like domains. The structure determined at 2.3 angstrom resolution reveals that the molecule has two tightly associated domains containing the immunoglobulin-fold connected by a continuous beta strand. The putative binding sites for monoclonal antibodies, class II MHC molecules and HIV gp120 (as determined by mutational analysis) map on the molecular surface (10, 11).

A soluble version of the entire extracellular segment of CD4 (V1–V4, termed sCD4) has been described and appears to be a potential therapeutic approach to the treatment of HIV infection (12). In vitro experiments demonstrate that: 1) SCD4 acts as a "molecular decoy" by binding to HIV gp120 and inhibiting viral attachment to and subsequent infection of human cells; 2) sCD4 "strips" the viral envelope glycoprotein gp120 from the viral surface; and 3) sCD4 blocks the intercellular spread of virus from HIV-infected cells to uninfected cells by inhibiting virus-mediated cell fusion (1, 13).

In addition to in vitro results, experiments with sCD4 in simian immunodeficiency virus (SIV)-infected rhesus monkeys have been described. These studies demonstrated that administration of 2 milligrams (intramuscular) of sCD4 for 28 days to SIV-infected rhesus monkeys led to a decreased ability to isolate virus from peripheral blood lymphocytes and bone marrow. In addition, the growth of granulocyte-macrophage and erythrocyte progenitor colonies in the bone marrow returned to normal levels. These data suggest that administration of sCD4 to SIV-infected rhesus monkeys leads to a diminution of the viral reservoir.

Phase I human clinical trials demonstrated that there is no significant toxicity or immunogenicity associated with administration of sCD4 at doses as high as 30 mg/day. Pharmacokinetic studies revealed the serum half-life of sCD4 to be 45 minutes following intravenous administration, 9.4 hours after intramuscular dosing, and 10.3 hours after the drug was given subcutaneously (14, 15). Preliminary antiviral studies were inconclusive with respect to CD4 cell count and levels of HIV antigen. Because the maximum tolerated dose was not reached, the antiviral effect of sCD4 may have been underestimated, especially in light of recent data concerning differences in sCD4 concentrations required to inhibit laboratory strains of HIV-1 compared to primary viral isolates (16).

Although these in vitro, primate, and human clinical studies with sCD4 have produced encouraging results, they have also defined several limitations. First, the measured serum half-life of sCD4 is relatively short. Second, sCD4 is monovalent with respect to gp120 binding in contrast with cell surface CD4 and viral surface gp120 which are multivalent. Third, sCD4 is not cytotoxic for HIV-infected cells. Fourth, sCD4 may not cross the placenta to a significant degree. Therefore, chimeric CD4 molecules have been described which take advantage of the immunoglobulin-like nature of CD4 and several beneficial properties of immunoglobulins themselves (i.e. CD4-immunoglobulin fusions).

Immunoglobulins, or antibodies, are the antigen-binding molecules produced by B lymphocytes which comprise the humoral immune response. The basic unit of an immunoglobulin molecule consists of two identical heavy chains and two identical light chains. The amino-terminus of each chain contains a region of variable amino acid sequence (variable region). The variable regions of the heavy and light chains interact to form two antigen binding sites. The carboxy-terminus of each chain contains a region of constant amino acid sequence (constant region). The light chain contains a single constant domain, whereas the heavy chain constant domain is subdivided into four separate domains (CH1, hinge, CH2, and CH3). The heavy chains of immunoglobulin molecules are of several types, including mu (M), delta (D), gamma (G), alpha (A) and epsilon (E). The light chains of immunoglobulin molecules are of two types, either kappa or lambda. Within the individual types of heavy and light chains exist subtypes which may differ in effector function. An assembled immunoglobulin molecule derives its name from the type of heavy chain that it possesses.

The development of monoclonal antibodies has circumvented the inherent heterogeneity of antibodies obtained from serum of animals or humans. However, most monoclonal antibodies are derived from cells of mouse origin and therefore are immunogenic when administered to humans. More recent developments combining the techniques of molecular genetics with monoclonal antibody technology has lead to the production of "humanized" chimeric antibodies in vitro. In these chimeric antibodies, the variable domains of human immunoglobulin heavy and light chains are replaced with specific heavy and light chain variable domains from a murine monoclonal antibody (17–19). The result of this genetic manipulation is a molecule with specificity for a particular antigen and the characteristics of human immunoglobulins.

Sequence and structural analyses of CD4 indicate that the four extracellular domains are immunoglobulin-like. Since the Fc portion of immunoglobulins controls the rate of catabolism of the molecules (serum half-life ranging from 14 to 21 days) and provides various effector functions, several reports describe the replacement of variable and constant domains of immunoglobulins with the immunoglobulin-like domains of CD4 (21–24).

CD4-IgG1 heavy chain fusion proteins resulting in chimeric gamma1 heavy chain dimers have been described (21). These molecules contain the gamma1 heavy chain CH1 domain in addition to the hinge, CH2 and CH3 domains. However, heavy chain assembly and secretion from mammalian cells is less efficient if the CH1 domain is expressed in the absence of light chains (25). Subsequently, a CD4-IgG1 heavy chain fusion protein lacking the CH1 domain and the first five amino acids of the hinge region was described which was secreted to high levels (22). These fusion proteins retain various effector functions of immunoglobulin molecules, such as Fc receptor binding, antibody-dependent cell-mediated cytotoxicity (ADCC) toward HIV-1-infected cells, and placental transfer via an Fc receptor-dependent mechanism (22). CD4-IgM heavy chain fusion proteins have also been described (26). In addition, CD4-IgG1 fusion proteins have been described wherein the V1V2 domains of CD4 are fused to the CH1, hinge, CH2 and CH3 domains of a gamma1 heavy chain, and wherein the V1V2 domains of CD4 are fused to the constant domain of a kappa light chain (29).

Fusion proteins linking CD4 to toxins have also been constructed and tested for their ability to kill HIV-infected cells. In one study, sCD4 was coupled to the deglycosylated A chain of ricin which inactivates ribosomes, therefore inhibiting protein synthesis and killing the cell (27). This fusion protein was reported to specifically lyse cells infected with five different isolates of HIV, but was nontoxic to uninfected cells. In another study, the V1V2 domains of CD4 were coupled to domains II and III of Pseudomonas exotoxin A (28). This fusion protein was reported to specifically bind and inhibit protein synthesis in cells expressing the HIV envelope glycoprotein gp120 (25).

It is well established that human monocytes and macrophages (M/M) express surface CD4, can be infected by HIV, and serve as a reservoir of infection and a vehicle for viral dissemination (29). Furthermore human M/M also contain Fc receptors, which are responsible for binding to specific IgG molecules via their Fc portion (see Table 1). The high affinity Fc receptor (FcRI) binds monomeric IgG and complexed IgG (antigen plus antibody). The rank order of affinity of FcRI for IgG isotypes is IgG1=IgG3>IgG4, and does not interact with IgG2. The low affinity Fc receptor (FcRII) binds monomeric IgG with lower affinity than IgG in complexed form. The rank order of affinity is that IgG1 and IgG3 binding is greater than that of IgG2 or IgG4 (30).

| FcReceptor | Molecular Weight | Affinity | Expression | Affinity for isotypes |
|---|---|---|---|---|
| FcRI | 72,000 | High | Monocytes | IgG1,IgG3> IgG4, does not bind IgG2 |
| FcRII | 40,000 | Low | Monocytes, platelets, neutrophils | IgG1,IgG3> IgG2, IgG4 |
| FcRIII | 50–70,000 | Low | Neutrophils NK, K, monocytes | IgG1,IgG3 |

(Table abbreviated from Gergely J. and Sarmay G. (1990) FASEB J. 4:3275

Because of the recent demonstration that HIV+ patients' sera contain low titer antibodies which recognize the HIV envelope glycoprotein, it has been observed that infection of M/M is enhanced by low titer anti-HIV antibodies, presumably by cross bridging HIV and the Fc receptor (31). Enhanced infection of macrophages by Dengue virus, Yellow fever virus, and Sindbis virus, is well documented in vitro as well as in Rhesus monkeys (32). Such enhancement has been demonstrated to occur in the presence of subneutralizing antibodies to these viruses, which serves to opsonize the viruses and bind them to the FcRs (or complement receptors) on the surface of the cell. In the case of HIV, this crossbridging serves to concentrate HIV onto the surface of the M/M, whereupon the virus is then able to utilize CD4 for entry into the cell, since sCD4 is able to inhibit the enhancement seen with low titer antibodies (31).

Recently, Byrn et al. (22) have produced a CD4-IgG chimera of the IgG1 isotype, to increase the plasma half-life of sCD4 as well as to confer effector functions to the chimeric molecule. Therefore this molecule has the potential to bind to Fc receptors located on the surface of the M/M, and potentially cause an increase in the infection of these cell types. Because enhanced infection of these cell types is a serious consideration in developing novel therapeutics, our objective for designing a CD4-IgG molecule was to use the IgG2 type, which has a greatly diminished ability to bind M/M Fc receptors (30). Furthermore, human IgG2 antibodies appear to lack significant allotypic variation, whereas human IgG1 antibodies contain allotypic variations (33). Therefore, to avoid potential immunogenic responses to recombinant molecules containing immunoglobulin domains, we have chosen a molecule which is the least polymorphic and has a decreased ability to concentrate HIV onto the surface of the macrophage.

Second, similar observations of enhanced infection of unborn babies may also be demonstrated for CD4-IgG1 immunoadhesions administered to pregnant mothers. For example, it is well documented that the placental syncytiotrophoblast plasma membrane contains Fc receptors (30). Because materno-fetal transport of immunoglobulin is primarily restricted to the IgG class, it is believed that passive immunity can be achieved by specific transport across the placenta via a specific Fc receptor transcytotic mechanism. Further, it appears that the Fc receptors on the placental syncytiotrophoblast membrane are selective in that immunoglobulins of the IgG1 type have approximately 10–20 fold higher binding affinity for the receptor. In fact, of all the IgG subtypes, IgG1 and 3 have the highest affinity for the receptor, followed by IgG4, and finally IgG2 (30). These results are consistent with those obtained from the cloning of the FcR from a human placenta, which indicate that the receptor is very similar to the FcRII type found on M/M. Although one might argue that transplacental transport of immunoglobulin may be beneficial to the fetus in utero, it could also be argued that specific maternal immunoglobulin raised to a specific pathogen (such as HIV), might facilitate transport across the placenta via an Fc dependent mechanism, to increase infection of the fetus, similar to the mechanism which has evolved to transport IgA across epithelia, via the poly Ig receptor (34). Thus specific CD4-IgG1 fusion proteins, which have been demonstrated to cross the placenta and concentrate in the fetal blood (22), may be detrimental to the fetus, by providing HIV with a novel mechanism to cross the placental barrier.

We have now discovered that a specific-CD4-gamma2 chimeric heavy chain homodimer provides advantages relative to those CD4-IgG1 heavy chain homodimers which have been described more than one year ago. Specifically, we have constructed a CD4-gamma2 chimeric heavy chain homodimer which contains the V1V2 domains of CD4 and which is efficiently assembled intracellularly and efficiently secreted from mammalian cells as a homodimer, enabling high recovery and purification from the medium of cells expressing this chimeric heavy chain homodimer. To construct this homodimer, we have used the entire hinge, CH2, and CH3 domains from a human gamma2 heavy chain, which results in a chimeric molecule containing the constant domains of a human IgG2 molecule responsible for dimerization and efficient secretion. This is in contrast to the heavy chain dimers described by Capon and Gregory (20) which include the CH1 domain in the CD4-IgG1 heavy chain dimer, resulting in poor secretion and recovery from cell culture medium of the recombinant molecule. We have also included the entire hinge domain of gamma2 heavy chain in the CD4-gamma2 chimeric heavy chain homodimer of this invention to provide efficient dimerization, since the cysteine residues contained in this domain are responsible for forming the disulphide links to the second chain of the homodimer, positioning the two chains in the correct spatial alignment and facilitating formation of the antigen combining site.

Furthermore, by including the entire hinge domain, we have maintained the segmental flexibility of the heavy chain dimers, thus enabling modulation of biological function such as complement activation and Fc receptor binding (29).

Since IgG2 immunoglobulins have a greatly diminished ability to bind to Fc receptors on monocytes, macrophages, and placental membranes, construction of a CD4-gamma2 chimeric heavy chain homodimer and a CD4-IgG2 chimeric heterotetramer results in chimeric proteins with many advantages that CD4-gamma1 chimeric heavy chain homodimers or CD4-IgG1 chimeric heterotetramers may not possess (20, 23, 24, 26). Furthermore, human IgG2 is significantly less polymorphic than other IgG types and therefore is less likely to be immunogenic when administered to humans. This is in contrast to human IgG1 which contains many allotypes and has a higher probability of being immunogenic when administered to humans.

In addition to the CD4-gamma2 chimeric heavy chain homodimers, we have also constructed CD4-IgG2 heavy chains, which contain the V1V2 domains of CD4 fused to the CH1, hinge, CH2 and CH3 domains of human gamma2 heavy chain. These molecules encode a CD4-IgG2 chimeric heterotetramer, and when co-expressed in the presence of CD4-kappa chimeric light chains containing the V1 and V2 domains of CD4 fused to the entire constant domain of human kappa light chains (or lambda light chains), enable the production of said heterotetramer. This heterotetramer comprises two CD4-IgG2 chimeric heavy chains and two CD4-kappa chimeric light chains. Producing heavy chains which contain the CH1 domain enables efficient association with the CD4-kappa chimeric light chains, resulting in efficient secretion of a CD4-IgG2 chimeric heterotetramer. These CD4-IgG2 chimeric heterotetramers possess increased serum half-lives and increased avidity for HIV as compared with heavy chain dimers.

SUMMARY OF THE INVENTION

This invention provides an expression vector encoding a CD4-gamma2 chimeric heavy chain homodimer. This invention also provides an expression vector encoding the heavy chains of a CD4-IgG2 chimeric heterotetramer. Finally, this invention provides an expression vector encoding the light chains of a CD4-IgG2 chimeric heterotetramer.

sequence of human CD4; V1V2, amino-terminal variable-like domains of human CD4; H, hinge region of human gamma2 heavy chain; CH2 and CH3, second and third constant regions of gamma2 heavy chain.

FIG. 2: A) Domain structure of chimeric genes used to express CD4-IgG2 chimeric heterotetramer. Top, CD4-gamma2 chimeric heavy chain gene; Bottom, CD4-kappa chimeric light chain gene. B) Protein structure of CD4-IgG2 chimeric heterotetramer. Abbreviations: CH1-CH2-CH3, first, second and third constant regions of human gamma2 heavy chain; C-kappa, constant region of human kappa light chain.

FIG. 3: DNA and predicted protein sequence of a CD4-gamma2 chimeric heavy chain homodimer (one chain SEQ ID NO. 2-3). The numbers at the end of each line indicate the nucleotide positions. The numbers above each line indicate the amino acid positions (given in single letter code). The protein domains are indicated above the sequences by arrows.

Figure 4:
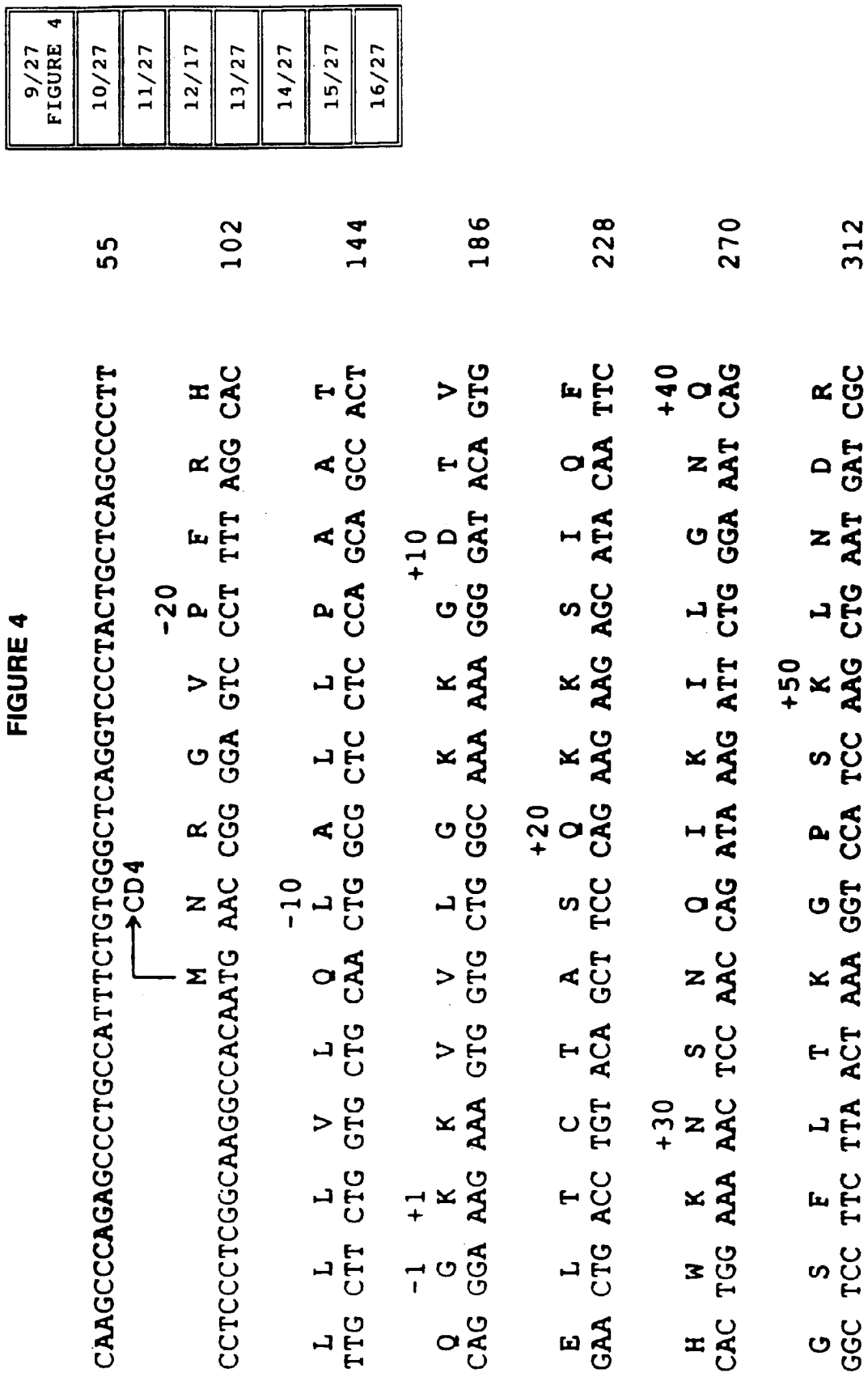

FIG. 4: DNA and predicted protein sequence of a CD4-IgG2 chimeric heavy chain of the CD4-IgG2 chimeric heterotetramer (SEQ ID NO. 4-5). The numbers at the end of each line indicate the nucleotide positions. The numbers above each line indicate the amino acid positions (given in single letter code). The protein domains are indicated above the sequences by arrows.

FIG. 5: DNA and predicted protein sequence of a CD4-kappa chimeric light chain of the CD4-IgG2 chimeric heterotetramer (SEQ ID NO. 6-7). The numbers at the end of each line indicate the nucleotide positions. The numbers above each line indicate the amino acid positions (given in single letter code). The protein domains are indicated above the sequences by arrows.

Figure 6:
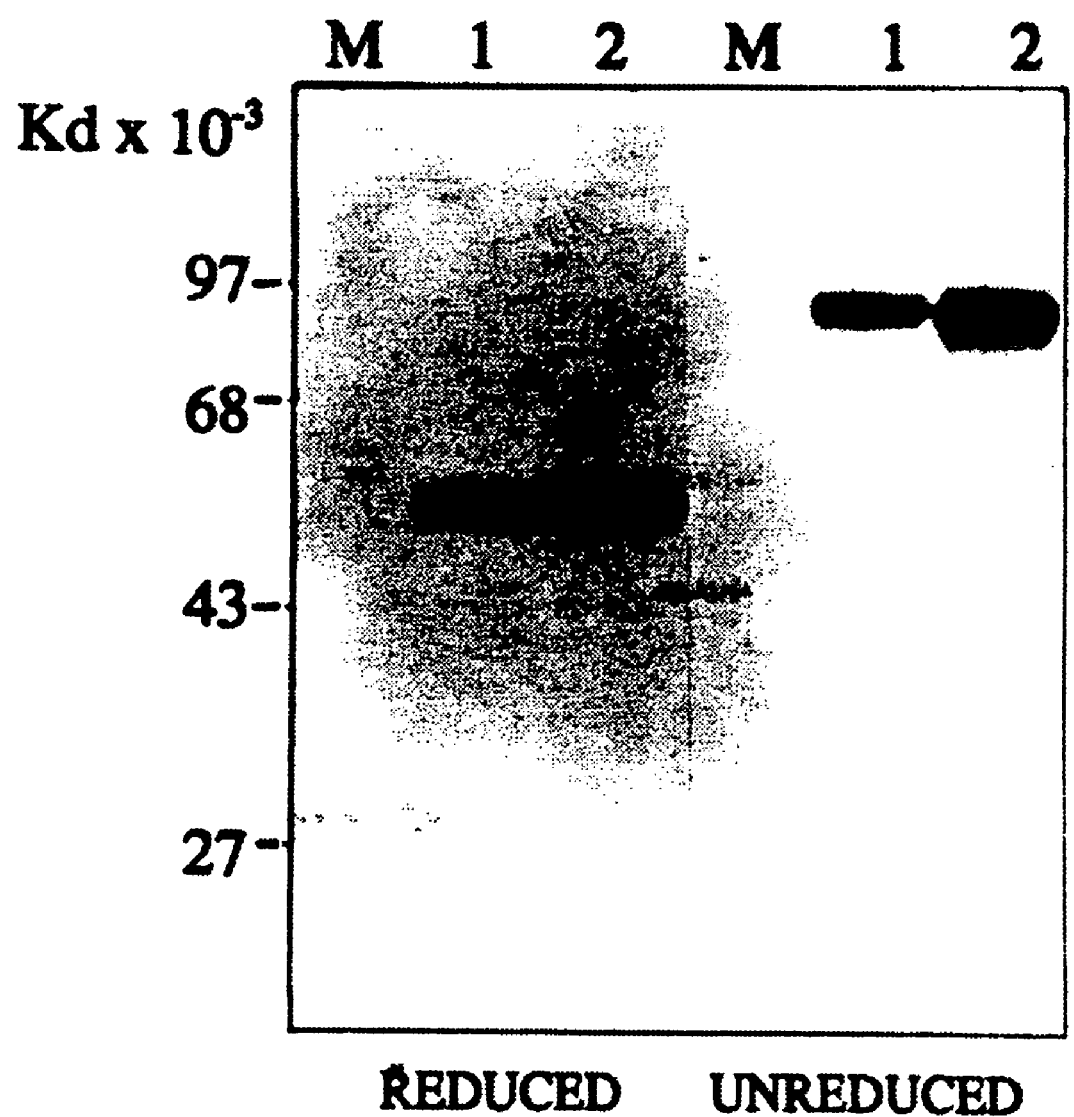

FIG. 6: Secretion of CD4-gamma2 chimeric heavy chain homodimer from transfected cells. Cos-M5 cells were mock transfected, transfected with CD4-gammal chimeric heavy chain mammalian expression vector DNA, or transfected with CD4IgG2-pcDNA1. At 48–72 hours post-transfection, the cells were radiolabelled with $^{35}$S-methionine. Radiolabelled medium was precipitated with Protein A-Sepharose® beads. The precipitated proteins were analyzed by SDS-PAGE under reducing or non-reducing conditions and were visualized by fluorography. Lane M, medium from mock transfected cells; Lane 1, medium from cells transfected with CD4-gammal chimeric heavy chain mammalian expression vector DNA; Lane 2, medium from cells transfected with CD4-IgG2-pcDNA1 DNA.

Figure 7:
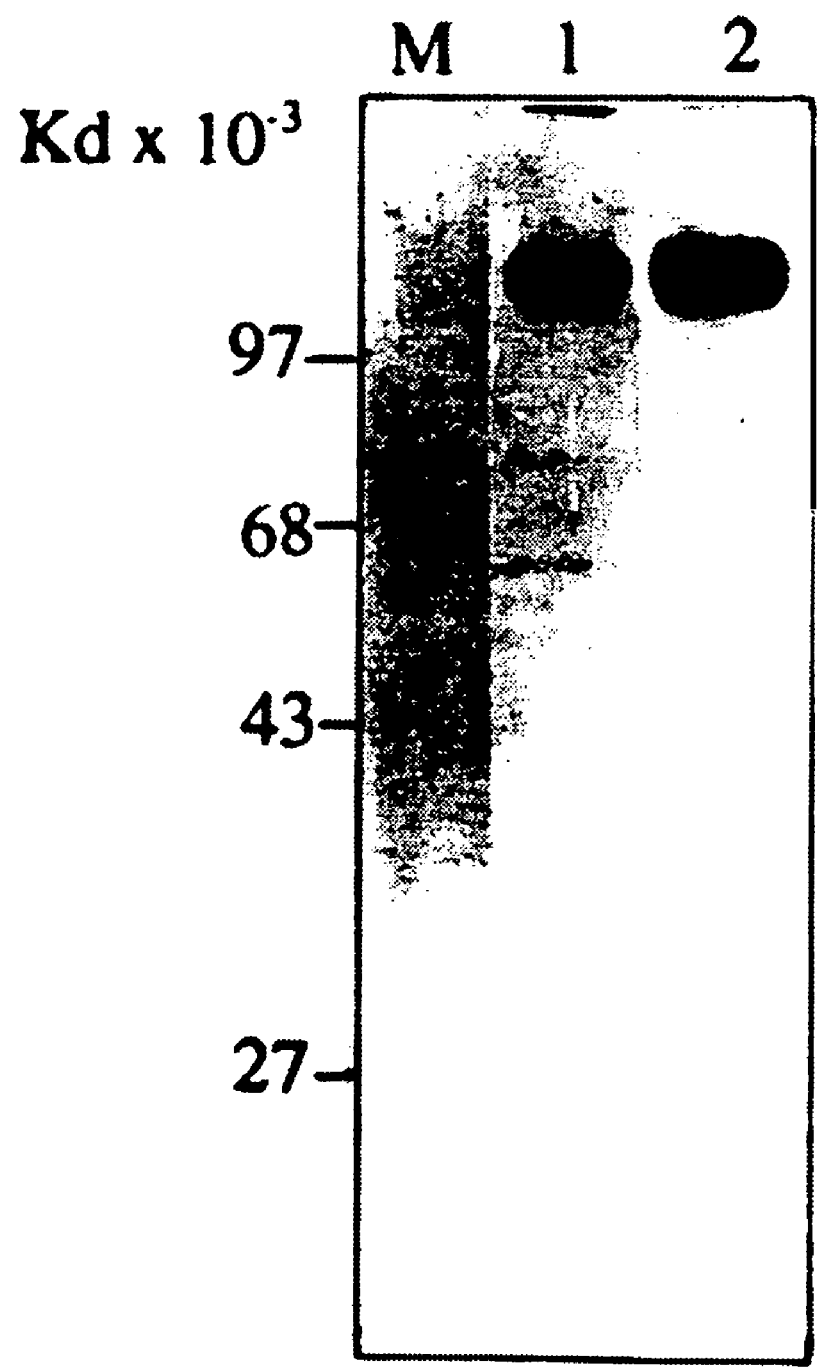

FIG. 7: Precipitation of HTV-1 gp120 with CD4gamma2 chimeric heavy chain homodimer. Cos-M5 cells were mock transfected, transfected with CD4-gammal chimeric heavy chain mammalian expression vector DNA, or transfected with the CD4-IgG2-pcDNA1. At 48–72 hours post transfection, unlabelled aliquots of medium were incubated with an aliquot of $^{35}$Smethionine labelled gp120. The complexes were precipitated with Protein A-Sepharose® beads. The precipitates were then analyzed by SDS-PAGE followed by fluorography. Lane M, medium from mock transfected cells; Lane 1, medium from cells transfected with CD4-gammal chimeric heavy chain mammalian expression vector DNA; Lane 2, medium from cells transfected with CD4-IgG2-pcDNA1 DNA.

Figure 8:
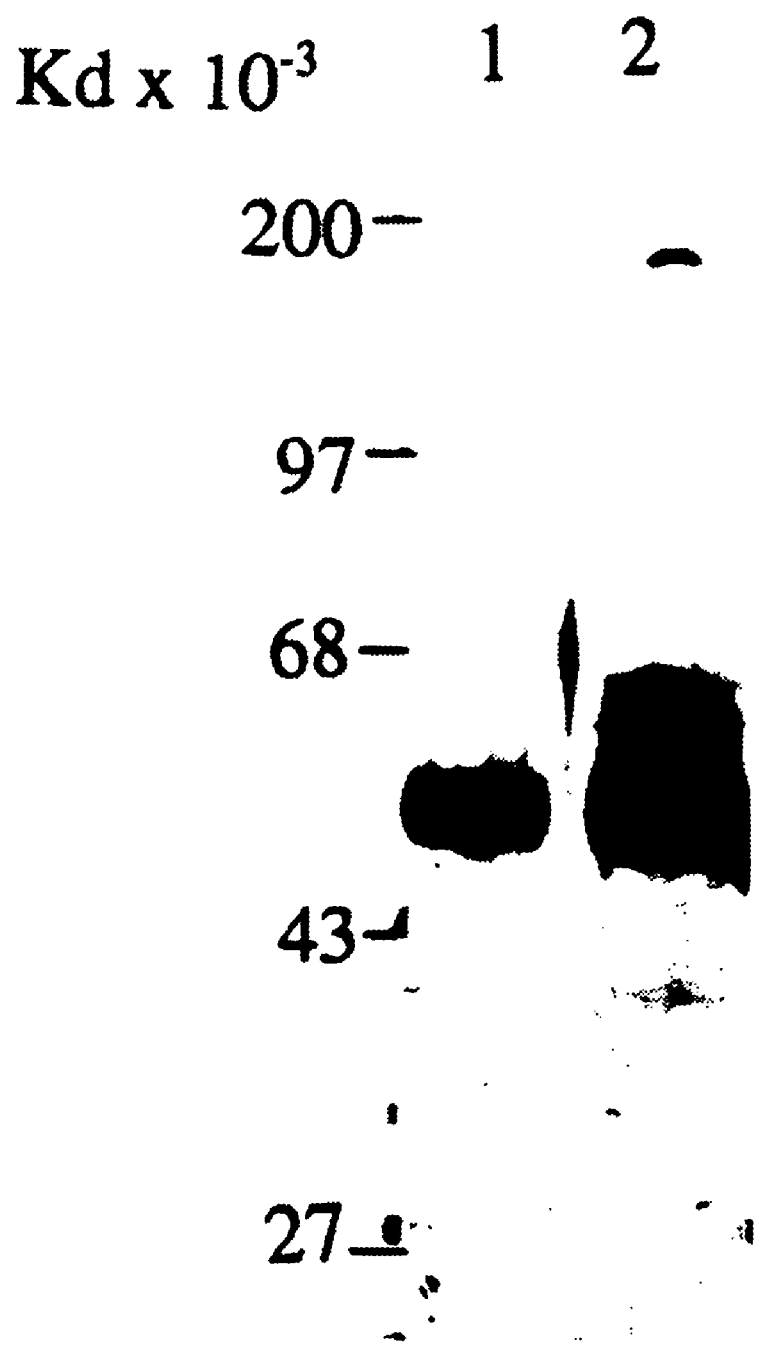

FIG. 8: Purification of CD4-gamma2 chimeric heavy chain homodimer from CHO cell-conditioned medium. Stable CHO cells constitutively secreting CD4-gammal chimeric heavy chain homodimer, or CD4-gamma2 chimeric heavy chain homodimer, were grown in roller bottles. Conditioned medium was passed over a Protein A-Sepharose® column and bound material was eluted from the column. The peak fractions were identified by SDS-PAGE followed by silver staining and pooled. The purified proteins were then analyzed by SDS PAGE under reducing conditions followed by silver staining.

Figure 9:
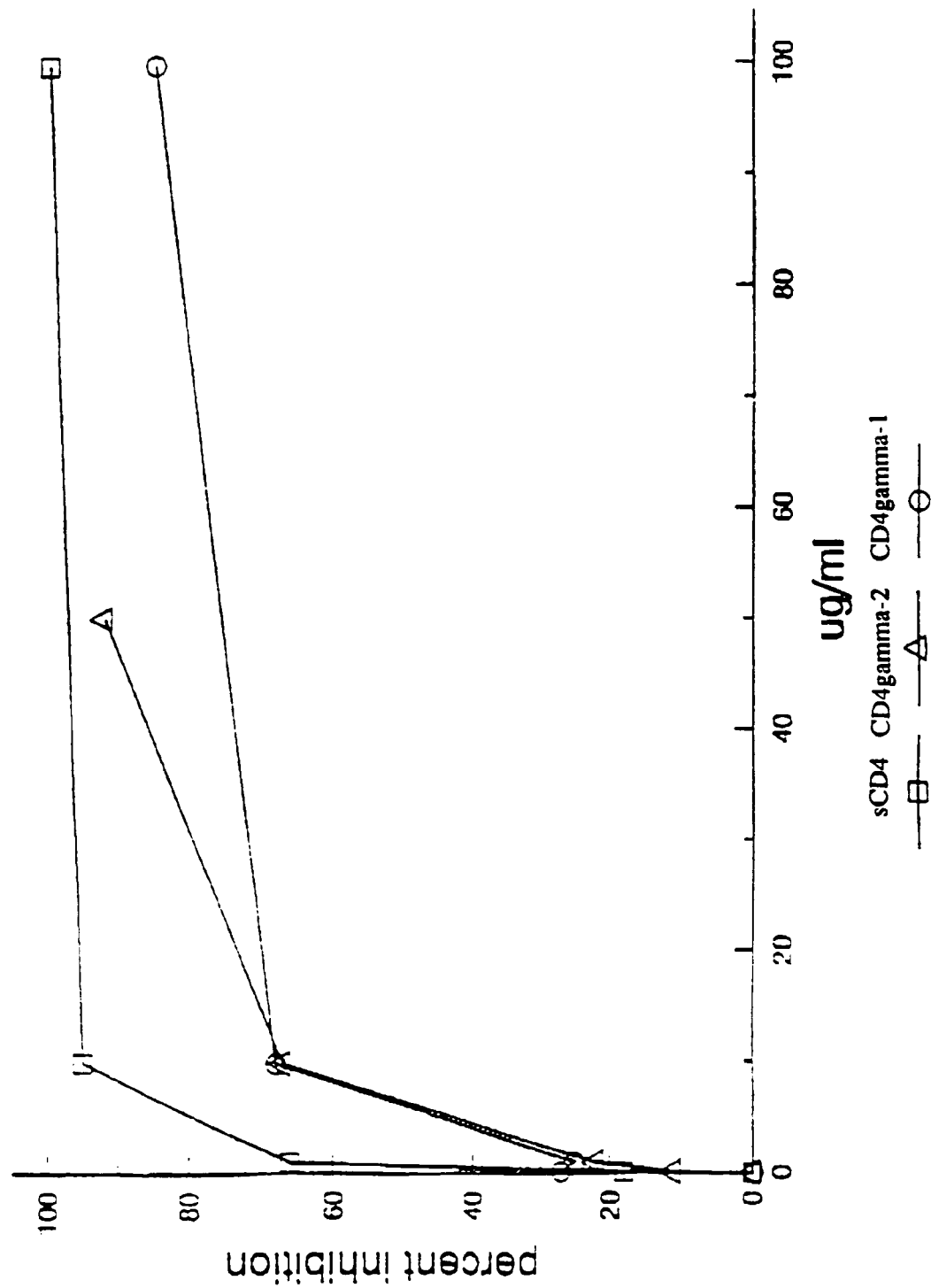

FIG. 9: Inhibition of HIV binding to CEM cells by CD4-based molecules. Soluble CD4 (sCD4), partially purified CD4-gammal, or partially purified CD4-gamma 2 were tested for inhibition of virus binding to CD4-positive cells. Bound virus was detected by indirect immunofluorescence and cytofluorography. Results are expressed as percent inhibition versus concentration of inhibiting agent.

Figure 10:
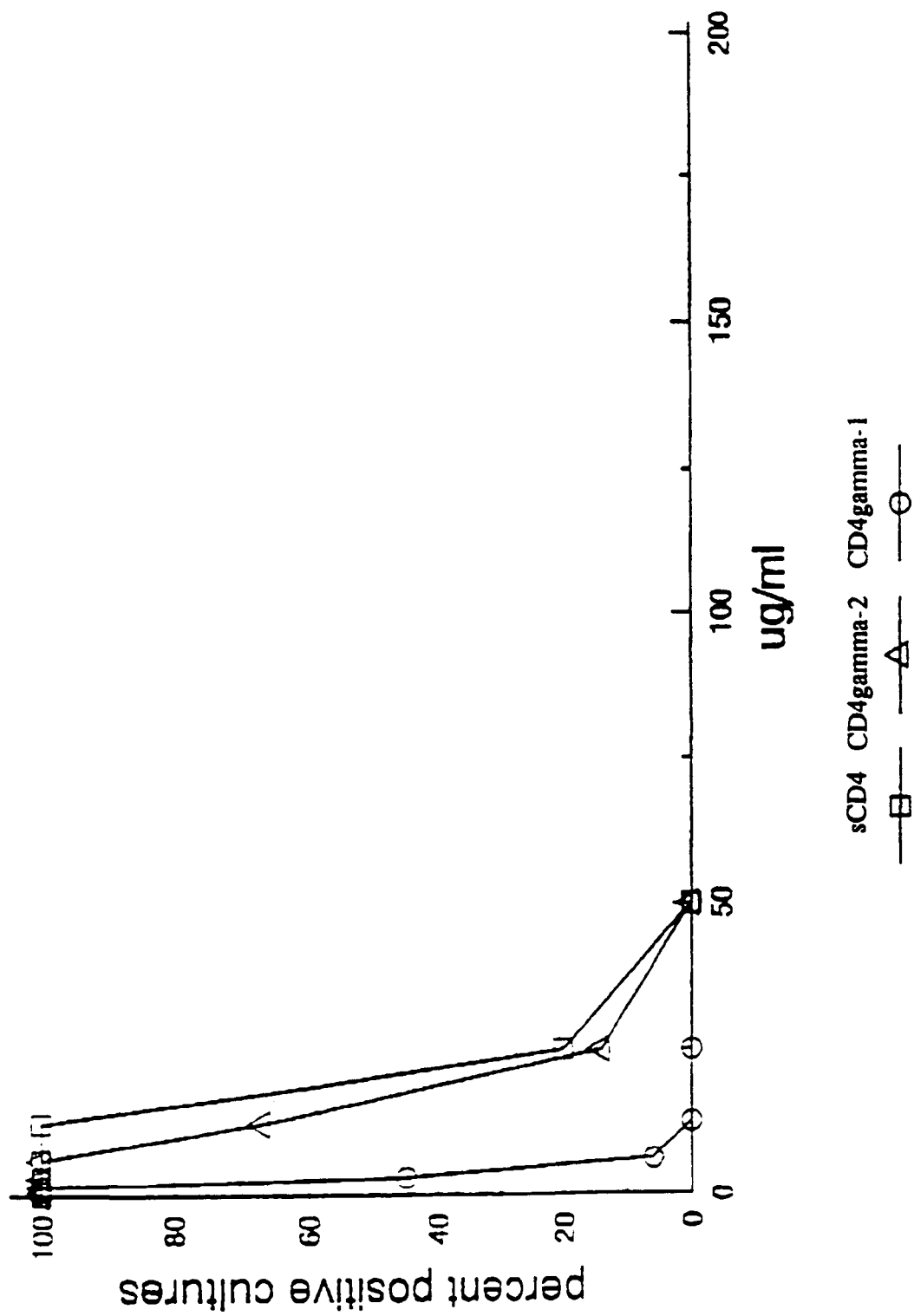

FIG. 10: Inhibition of HIV infection of CD4-positive cells by CD4-based molecules. sCD4, partially purified CD4-gammal, or partially purified CD4-gamma2 were incubated with an HIV-1 inoculum (100 TCID$_{50}$), and mixtures were added to PHA-stimulated lymphocytes and incubated at 37° C. overnight. The cells were washed and plated in microculture (1×10$^5$ cells/culture; 10 cultures per dilution) and monitored for reproductive viral replication by detection of HIV antigen in culture supernates 8 and 12 days later. Results are expressed as percent positive cultures at a given concentration of inhibiting agent.

Figure 11:
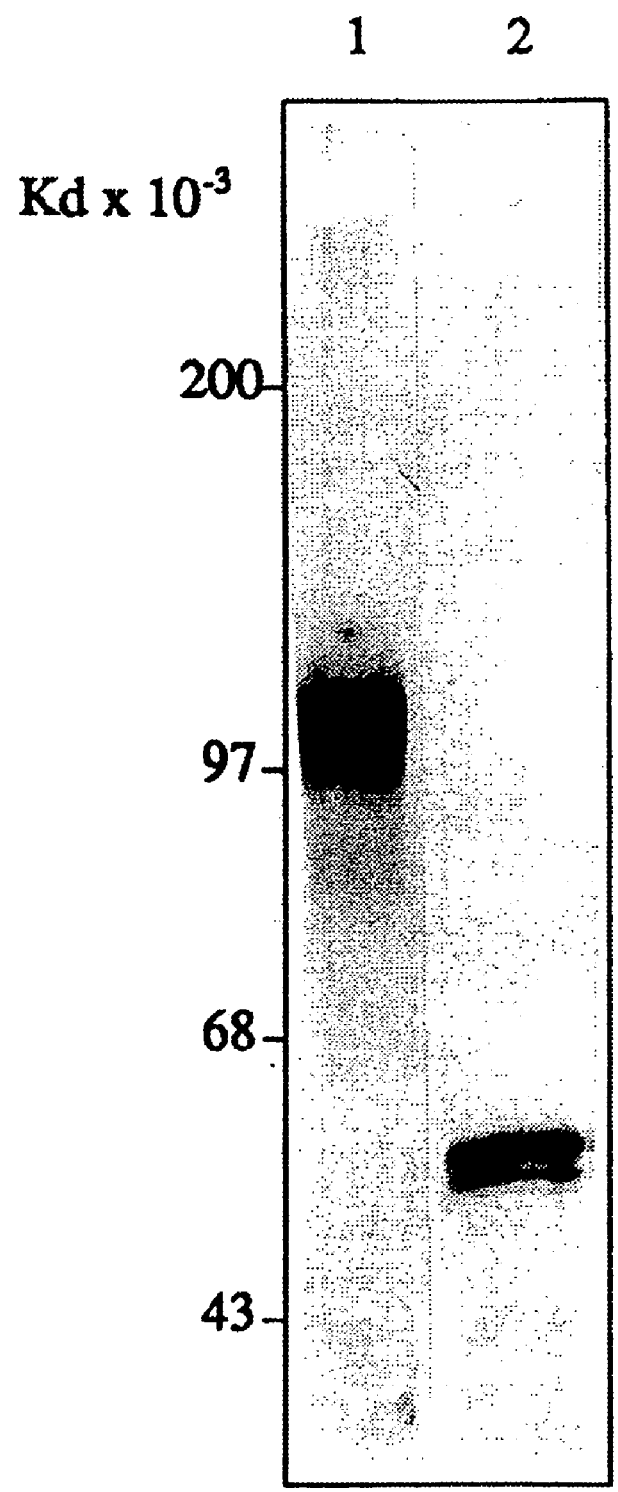

FIG. 11: Purification of CD4-gamma2 chimeric heavy chain homodimer. Stable CHO cells constitutively secreting CD4-gamma2 chimeric heavy chain homodimer were grown in roller bottles. Conditioned medium was passed over a Protein A A-Sepharose® column and bound material was eluted from the column (see FIG. 8). The peak fractions were then pooled and passed over an S-Sepharose® column. After extensive washes, the CD4-gamma2 chimeric heavy chain homodimer was eluted with 50 mM BES pH 7.0, 500 mM NaCl. The peak fractions were identified by SDS-PAGE followed by silver staining, pooled, and concentrated. The pooled, concentrated CD4-gamma2 chimeric heavy chain homodimer was then applied to a Sephacryl® S-300RR column preequilibrated and run with PBS.

The peak fraction corresponding to purified CD4-gamma2 chimeric heavy chain homodimer was identified by SDS-PAGE followed by silver staining. The peak fractions were then pooled and concentrated. The purified protein was then analyzed by SDS-PAGE under non-reducing and reducing conditions followed by silver staining. Lane 1: approximately 1.5 µg protein run under non-reducing conditions, Lane 2: approximately 1.5 µg protein run under reducing conditions.

FIG. 12: Secretion of CD4-IgG2 chimeric heterotetramer from stably transfected cells. CHO cells stably expressing both CD4-IgG2 chimeric heavy chains and CD4-kappa chimeric light chains were radiolabelled with $^{35}$S-methionine and cysteine. Radiolabelled medium was precipitated with Protein A-Sepharose® beads. (A) The precipitated proteins were analyzed by SDS-PAGE under non-reducing conditions, and were visualized by fluorography. Lane 1: medium from untransfected CHO cells, Lane 2: medium from cells stably expressing both the CD4-IgG2 chimeric heavy chains, and CD4-kappa chimeric light chains. (B) An identical sample to that run in lane 2 from (A) was run on SDS-PAGE under nonreducing conditions. The lane from this SDS-PAGE gel was excised and the proteins reduced by incubation of the gel slice for 45 minutes at 4° C. in equilibration buffer (62.5 mM TrisHCl pH 6.8, 2.3% SDS, 5% β-mercaptoethanol, 10% glycerol). After incubation of the gel slice under reducing conditions, the proteins contained within the gel were analyzed by SDS-PAGE and visualized by fluorography.

DETAILED DESCRIPTION OF THE INVENTION

Five expression vectors and two plasmids designated CD4-IgG2-Rf, CD4-IgG1-Rf, CD4-IgG1HC-pRcCMV, CD4-IgG2HC-pRcCMV, CD4-kLC-pRcCMV, CD4-IgG1-pcDNA1, and CD4-IgG2-pcDNA1, respectively have been deposited with the American Type Culture Collection, 10801 University Boulevard, Manassas, Va. 20110-2209, under ATCC Accession Nos. 40949, 40950, 75192, 75193, 75194, 40951, and 40952, respectively. These deposits were made pursuant to the provisions of the Budapest Treaty on the International Recognition of the Deposit of Microorganisms for the Purposes of Patent Procedure (Budapest Treaty). The deposits with ATCC Designation Nos. 40949, 40950, 40951, and 40952 were deposited on Jan. 31, 1991. The deposits with ATCC Designation Nos. 75192, 75193 and 75194 were deposited on Jan. 30, 1992.

Specifically, the invention provides an expression vector designated CD4-IgG2-pcDNA1 (ATCC No. 40952) encoding a CD4-gamma2 chimeric heavy chain homodimer. The invention additionally provides a CD4-gamma2 chimeric heavy chain homodimer encoded by this expression vector or any other expression vector having the same DNA coding region inserted therein. Specifically, the invention also provides expression vectors designated CD4-IgG2HC-pRcCMV (ATCC No. 75193), and CD4-kLC-pRcCMV (ATCC No. 75194), encoding a CD4-IgG2 chimeric heavy chain and a CD4-kappa chimeric light chain. The invention additionally provides a CD4-IgG2 chimeric heterotetramer encoded by these expression vectors or any other expression vector having the same DNA encoding region inserted therein.

In accordance with the invention, numerous vector systems for expression may be employed. For example, one class of vectors utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have stably integrated the DNA into their chromosomes may be selected by introducing one or more markers which allow selection of transfected host cells. The marker may provide for prototrophy to an auxotrophic host, biocide resistance, e.g., antibiotics, or resistence to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by Okayama. (37)

Thus, the invention further provides a method of producing CD4-gamma2 chimeric heavy chain homodimer. This method comprises
 a) transfecting a mammalian cell with an expression vector for producing the CD4-gamma2 chimeric heavy chain homodimer;
 b) culturing the resulting transfected mammalian cell under conditions such that CD4-gamma2 chimeric heavy chain homodimer is produced; and
 c) recovering the CD4-gamma2 chimeric heavy chain homodimer so produced.

Once the vector or DNA sequence containing the constructs has been prepared for expression, the expression vectors may be transfected or introduced into an appropriate mammalian cell host. Various techniques may be employed such as protoplast fusion, calcium phosphate precipitation, electroporation or other conventional techniques. In the case of protoplast fusion, the cells are grown in media and screened for the appropriate activity. Expression of the gene(s) results in production of the fusion protein which corresponds to one chain of the CD4-gamma2 chimeric heavy chain homodimer. This fusion protein may then be treated to form the chimeric heavy chain homodimer.

Further, methods and conditions for culturing the resulting transfected cells and for recovering the chimeric heavy chain homodimer so produced are well known to those skilled in the art and may be varied or optimized depending upon the specific expression vector and mammalian host cell employed.

In accordance with the claimed invention, the preferred host cells for expressing the chimeric heavy chain homodimers of this invention are mammalian cell lines, including, for example, monkey kidney CV1 line transformed by SV40 (COS-7); human embryonic kidney line 293; baby hamster kidney cells (BHK) Chinese hamster ovary-cells-DHFR (CHO); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127) and myeloma cell lines.

The invention further provides a method of inhibiting the HIV infection of a CD4+ cell which comprises treating the CD4+ cell with the CD4-gamma2 chimeric heavy chain homodimer in an amount which is effective to inhibit infection of the cell.

Additionally, the invention provides a method of preventing a subject from being infected with HIV which comprises administering to the subject the CD4-gamma2 chimeric heavy chain homodimer in an amount which is effective to prevent the subject from being infected with HIV.

Although the invention encompasses the administration of the chimeric heavy chain homodimer to various subjects, AIDS patients are of particular interest. Further, methods of administering the homodimer are well known in the art and include, merely by way of example, subcutaneous, intramuscular and intravascular injection, alone or in combination with other agents such as AZT or DDI.

Further provided is a method of treating a subject infected with HIV so as to block the spread of HIV infection which comprises administering to the subject an amount of the CD4-gamma2 chimeric heavy chain homodimer in an amount which is effective to block the spread of HIV infection.

For example, the homodimer may be administered to patients having HIV infection at a dosage capable of maintaining a concentration of greater than about 100 ng of CD4-gamma2 chimeric heavy chain homodimer/ml plasma. For CD4-gamma2 chimeric heavy chain homodimer variants having different molecular weights, about 2 picomoles of soluble receptor per ml of plasma, an amount for example, sufficient to establish a stoichiometric equivalence with native (membrane bound) and soluble receptor is administered. Typically, the dosage of soluble CD4 is about 100 µg/kg of patient weight/day.

The foregoing method may be used to help prevent the spread of the HIV virus within the body of a HIV infected patient. Additionally, CD4-gamma2 chimeric heavy chain homodimer may be administered as a prophylactic, measure to render a subject's blood less susceptible to the spread of the HIV virus. Such prophylactic administration includes administration both prior to HIV contact or shortly thereafter, or both.

A pharmaceutical composition which comprises the CD4-gamma2 chimeric heavy chain homodimer of thus invention in an amount effective to inhibit HIV infection of a CD4+ cell and a pharmaceutically acceptable carrier is further provided.

Pharmaceutically acceptable carriers are well known in the art to which the present invention pertains and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, anti-microbials, antioxidants, chelating agents, inert gases and the like. (38)

The invention further provides a composition of matter comprising a CD4-gamma2 chimeric heavy chain homodimer and a toxin linked thereto.

Some example of toxins are the deglycosylated A chain of ricin, domains II or III of *Pseudomonas* exotoxin A, *Diphtheria* toxin, or a non-peptidyl cytotoxin. These toxins may be linked using conventional in vitro protein, cross-linking agents (39–41). Additionally the toxins may be linked by recombinant synthesis as a fusion protein (see for example U.S. Pat. No. 4,765,382).

The invention also provides a diagnostic reagent comprising a CD4-IgG2 chimeric heavy chain homodimer and a detectable marker linked thereto. By employing a molecule which binds to the HIV virus and additionally has attached, to it a detectable marker, one may identify cells which are infected with HIV. Examples of conventional detectable markers includes radioisotopes such as I125, chromophores, and fluorophores.

Thus, the chimeric heavy chain homodimer of the invention may be used in an assay for HIV or SIV viral infection in a biological sample by contacting a sample derived from an animal suspected of having an HIV or SIV infection, with the homodimer of the invention, and detecting whether a complex forms with gp120, either alone or on the surface of an HIV-infected cell. For this purpose the homodimer may be labeled with a detectable marker or may be unlabeled and then be detected with another reagent which is detectably labeled and is specifically directed to the homodimer or to a complex between it and gp120.

For example, a biological sample may be treated with nitro-cellulose, or another solid support which is capable of immobilizing cells, cell particles or soluble protein. The support may then be washed with suitable buffers followed by treatment with the chimeric heavy chain homodimer which may be detectably labeled. The solid phase support may then be washed with buffer a second time to remove unbound fusion protein and the labeled homodimer detected.

In carrying out the assay the following steps may be employed.

a) contacting a sample suspected of containing gp120 with a solid support to effect immobilization of gp120, or cells which express gp120 on their surface;

b) contacting said solid support with the detectably labeled chimeric heavy chain homodimer of the invention;

c) incubating said detectably labeled homodimer with said support for a sufficient amount of time to allow the homodimer to bind to the immobilized gp120 or cell which expresses gp120 on its surface;

d) separating the solid phase support from the incubation mixture obtained in step c); and e) detecting bound labeled homodimer and thereby detecting gp120.

Such a method may be formatted either as a qualitative or as a quantitative test using methods well known in the art.

Alternatively, labeled homodimer-gp120 complex may be separated from a reaction mixture by contacting the complex with an immobilized antibody or protein which is specific for an immunoglobulin or, e.g., protein A, protein G, or anti-IgG antibodies. Such anti-immunoglobulin antibodies may be monoclonal or polyclonal. The solid support may then be washed with suitable buffers to obtain an immobilized gp120-labeled homodimer-antibody complex. The label on the homodimer may then be detected so as to measure endogenous gp120, and thereby detect the presence of HIV.

In one embodiment of the invention, a method for detecting HIV or SIV viral infection in a sample is provided comprising:

a) contacting a sample suspected of containing gp120 with a CD4-gamma2 chimeric heavy chain homodimer in accordance with this invention, and the Fc portion of an immunoglobulin chain; and b) detecting whether a complex is formed.

The invention also provides a method of detecting gp120 in a sample comprising:

a) contacting a mixture obtained by contacting a sample suspected of containing gp120 with a homodimer of this invention, and the Fc portion of an immunoglobulin chain, with an Fc binding molecule, such as an antibody, protein A, or protein G, which is immobilized on a solid phase support and is specific for the homodimer, to obtain a gp120-homodimer immobilized antibody complex, b) washing the solid phase support obtained in step (a) to remove unbound homodimer; and c) detecting the homodimer.

Of course, the specific concentrations of unlabeled or detectably labeled homodimer and gp120, the temperature and time of incubation, as well as other assay conditions, may be varied depending on various factors including the concentration of gp120 in the sample, the nature of the sample, and the like. Those skilled in the art are readily able to determine operative and optimal assay conditions for each determination.

Also provided is an enzyme-linked immunoadsorbent assay (ELISA) to detect and quantify soluble CD4 (sCD4) or CD4 chimeric proteins. In carrying out the assay, the process comprises:

a) contacting a sample containing sCD4 with a solid support to immobilize soluble sCD4;

b) contacting said solid support with the detectably labeled monoclonal antibody OKT4a alone, or with a sample containing sCD4 or CD4 chimeric proteins and OKT4a;

c) incubating said detectably labeled OKT4a containing media for sufficient time to allow for binding to immobilized SCD4;

d) separating the solid phase support from the incubation mixture in step (c);

e) detecting the bound OKT4a and thereby quantifying the amount of CD4 contained in the sample.

The invention further provides an expression vector encoding the heavy chains of a CD4-IgG2 chimeric heterotetramer, designated CD4-IgG2HC-pRcCMV (ATTC No. 75193). The invention also provides a CD4-IgG2 chimeric heterotetramer, the heavy chains of which are encoded by this expression vector or another vector containing the same coding sequence.

Additionally, the invention provides an expression vector encoding the light chains of a CD4-IgG2 chimeric heterotetramer, designated CD4-kLC-pRcCMV (ATCC No. 75194). Finally, the invention provides a CD4-IgG2 chimeric heterotetramer, the light chains of which are encoded by the CD4-kLC-pRcCMV expression vector or another vector containing the same coding sequence.

Further, the invention provides a CD4-IgG2 chimeric heterotetramer both the heavy and light chains of which are encoded by the aforementioned expression vectors.

The invention further provides a method of producing such a CD4-IgG2 chimeric heterotetramer. This method comprises:

a) cotransfecting a mammalian cell with the expression vector for producing the light chains of a CD4-IgG2 chimeric heterotetramer and an expression vector encoding a light chain;

b) culturing the resulting cotransfected mammalian cell under conditions such that CD4-IgG2 chimeric heterotetramer is produced; and c) recovering the CD4-IgG2 chimeric heterotetramer so produced.

Methods of cotransfecting mammalian cells are well known in the art and include those discussed hereinabove. Similarly, expression vectors encoding light chains are well known in the art.

The invention additionally provides a method of producing a CD4-IgG2 chimeric heterotetramer which comprises:

a) cotransfecting a mammalian cell with the expression vector for producing the light chains of a CD4-IgG2 chimeric heterotetramer and with an expression vector encoding an IgG1 heavy chain;

b) culturing the resulting cotransfected mammalian cell under conditions such that a CD4-IgG2 chimeric hetero-tetramer is produced; and c) recovering the CD4-IgG2 chimeric heterotetramer so produced.

Further the invention provides a method of producing an CD4-IgG2 chimeric heterotetramer which comprises:

a) cotransfecting a mammalian cell with the expression vector for producing the heavy chains of a CD4-IgG2 chimeric heterotetramer and an expression vector for producing the light chains of an CD4-IgG2 chimeric heterotetramer;

b) culturing the resulting cotransfected mammalian as cell under conditions such that the CD4-IgG2 chimeric heterotetramer is produced; and c) recovering the CD4-IgG2 chimeric heterotetramer so produced.

The invention also includes a method of inhibiting HIV infection of a CD4+ cell which comprises treating the CD4+ cell with either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV; or a CD4-IgG2 chimeric heterotetramer, both the heavy and the light chains of which are encoded by both of the above expression vectors, in an amount effective to inhibit infection of the cell.

The invention further provides a method of preventing a subject from being infected with HIV. This method comprises administering to the subject either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV; or a CD4-IgG2 chimeric heterotetramer, both the heavy and the light chains of which are encoded by the above expression vectors, in an amount which is effective to prevent the subject from being infected with HIV.

The invention also provides a method of treating a subject infected with HIV so as to block the spread of HIV infection. This method comprises administering to the subject either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV;.or a CD4-IgG2 chimeric heterotetramer, both the heavy and the light chains of which are encoded by the above-described expression vectors, in an amount effective to block spread of HIV infection, for example, within the subject or an AIDS patients body.

The invention also provides a pharmaceutical composition which comprises either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV, or a CD4-IgG2 chimeric heterotetramer, both the heavy and the light chains of which are encoded by the above-described expression vectors, in an amount effective to inhibit HIV infection of a CD4+ cell, and a pharmaceutically acceptable carrier.

Further provided by the invention is a composition of matter comprising either a CD4-IgG2 chimeric heterotetramer, the heavy chains of which are encoded by the expression vector designated CD4-IgG2HC-pRcCMV; a CD4-IgG2 chimeric heterotetramer, the light chains of which are encoded by the expression vector designated CD4-kLC-pRcCMV, or a CD4-IgG2 chimeric heterotetramer, both the heavy and the light chains of which are encoded by the above-described expression vectors, and a toxin linked thereto.

In one embodiment of the invention, the toxin is the deglycosylated A chain of ricin, domains II or III of *Pseudomonas* exotoxin A, *Diphtheria* toxin, or a non-peptidyl cytotoxin.

The invention further provides a diagnostic reagent either comprising a CD4-IgG2 chimeric heterotetramer, the heavy chains of which are encoded by the expression vector designated CD4-IgG2HC-pRcCMV; a CD4-IgG2 chimeric heterotetramer the light chains of which are encoded by the expression vector designated CD4-kLC-pRcCMV; or a CD4-IgG2 chimeric heterotetramer both the heavy and the light chains of which are encoded by both of those expression vectors, and a detectable marker linked thereto.

Examples of suitable detectable markers are radioisotopes, chromophores or fluorophores.

In order to facilitate understanding of the following examples, certain frequently occurring methods and/or terms are-best described in Maniatis et al. (42)

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

A. Materials and Methods

Figure 1A:
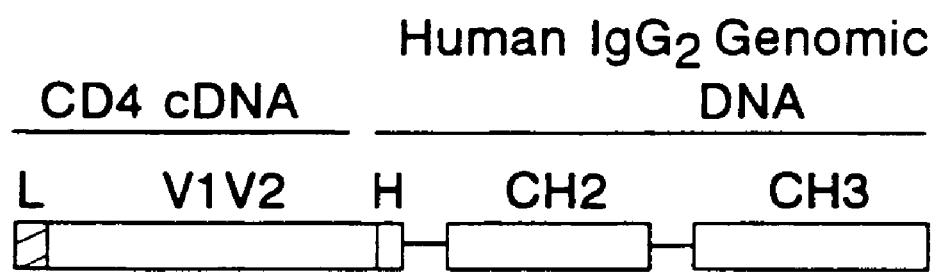
FIG. 1: A) Domain structure of CD4-gamma2 chimeric heavy chain gene; B) Protein structure of CD4-gamma2 chimeric heavy chain homodimer. The sequence shown below is the single letter amino acid code of the junction between CD4 (phe179) and the hinge region of human gamma2 heavy chain (SEQ ID NO. 1). Note that the hinge region of a gamma2 heavy chain contains four cysteines (see text for discussion). Abbreviations: L, leader (signal)

1. Construction of CD4-gamma2 Chimeric Heavy Chain Gene Encoding CD4-gamma2 Chimeric Heavy Chain Homodimer:

The human CD4 cDNA was excised from the plasmid pSP6T4 (4) as an EcoR1/Stu1 restriction fragment. The 0.70 kilobase fragment was isolated and cloned into EcoR1/Sma1 digested M13mp18. This intermediate vector (M13mp18 (CD4)) was then isolated, linearized with Pst1, purified, and treated with Bacterial Alkaline Phosphatase (BAP). The 2.0 Kb Pst1/Pst1 fragment from the plasmid pBr gamma2 containing the human gamma2 heavy chain gene (36) (containing the hinge, CH2, and CH3 exons) was isolated and cloned into the BAP-treated M13mp18/CD4 vector. Resulting recombinants were then screened for the correct orientation of the Pst1 fragment (with respect to the CD4 sequence) to obtain a vector which contains in tandem CD4 (EcoR1/Stu1)-gamma2 (Pst1/Pst1) To obtain a CD4-gamma2 chimeric heavy chain gene, oligonucleotide-mediated site-directed mutagenesis was performed to juxtapose the CD4 and gamma2 heavy chain DNA sequences, ligating the CD4 sequence in frame to the hinge exon. The resulting chimeric DNA molecule encodes a protein containing the V1V2 domains of CD4 followed by the hinge, CH2, and CH3 domains of gamma2 heavy chain (FIG. 1A) Mutagenesis was performed on single-stranded DNA isolated from recombinant phage from transformed TG1 cells (Amersham). Briefly, template DNA was annealed with a 34-mer oligonucleotide (5'-GACACAACATTTGCGCTC-GAAAGCTAGCACCACG-3'), containing sequences which join the last codon encoding Phe(179) from V1V2 of CD4 to the first codon of the hinge for IgG2 (encoding Glu) (FIGS. 1A and 3). After second strand synthesis, double stranded DNA was transformed into competent TG1 cells. Isolated plaques were then grown in fresh TG1 cells and single stranded DNA was purified for DNA sequencing. All mutations were verified and confirmed by dideoxy sequencing using the Sequenase® system (USB). Plaques containing the chimeric gene with the correct sequence were then grown in TG1 cells, and Rf DNA (designated CD4IgG2-Rf) was isolated from the cells.

2. Construction of Mammalian Expression Vector Encoding CD4-gamma2 Chimeric Heavy Chain Homodimer:

The CD4-gamma2 chimeric heavy chain gene was isolated from the recombinant Rf DNA following Rf linearization with EcoR1. The EcoR1 sites in the linearized DNA were filled in with the Klenow fragment of DNA polymerase I. The flush ended DNA was then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA was extensively digested with HindIII to liberate a fragment containing the CD4-gamma2 chimeric heavy chain gene. This HindIII fragment was then purified and ligated to the expression vector pcDNA-1 (Invitrogen), which was previously digested with HindIII and BAP treated. The resulting plasmid was then transformed into MC1061/P3 cells. Plasmid DNA was isolated from recombinant clones, and verification of the presence of the HindIII insert and orientation of the insert with respect to the cytomegalovirus (CMV) promoter in the plasmid was made by restriction enzyme analysis. The resulting mammalian expression plasmid which encodes a CD4-gamma2 chimeric heavy chain homodimer is designated CD4IgG2-pcDNA1.

3. Expression of CD4-IgG2-pcDNA1 in Mammalian Cells:

a. Transient Expression.

CosM5 cells grown in DMEM containing 10% fetal calf serum are split to 75% confluence. On the following day, the cells are transfected for 16–20 hours with 5 micrograms of CsCl-purified CD4-IgG2HC-pRcCMV DNA and 5 micrograms of CsCl-purified CD4-kLC-pRcCMV plasmid DNA by the standard $CaPO_4$ precipitation technique. After transfection, fresh medium is added to the cells. Analysis of the products synthesized 48–72 hours posttransfection is performed by radiolabelling of transfectants with $^{35}$S-methionine for 12–18 hours followed by precipitation of media and cell lysates using anti-CD4 antibodies or by incubation with Protein A-Sepharose® beads alone followed by SDS-PAGE under reducing or non-reducing conditions. In addition, analysis of media and cell lysates is performed 48–72 hours post-transfection by standard Western blotting procedures.

b. Stable Expression.

Dhfr-Chinese hamster ovary cells (CHO) were transfected with 20 micrograms of CsCl purified DNA in a 1000:1 molar ratio of CD4IgG2-pcDNA1:p410 (p410 is an expression plasmid containing the dhfr gene) although other ratios may also be used. Approximately 3–5 days post-transfection, cells were placed in selective medium (nucleoside-free alpha MEM containing 10% dialyzed fetal calf serum). Approximately 10–15 days post-selection, individual cell clones were picked and analyzed for stable expression of CD4-gamma2 chimeric heavy chain homodimer by several screening techniques, such as ELISA and precipitation with Protein A-sepharose beads followed by SDS-PAGE under reducing and non-reducing conditions. Clones expressing the highest levels were subjected to successive rounds of amplification of the newly introduced DNA sequences in increasing concentrations of methotrexate. Stable CHO cell lines were thus generated which secrete between 10–100 micrograms/milliliter of CD4-gamma2 chimeric heavy chain homodimer.

4. Purification of CD4-gamma2 Chimeric Heavy Chain Homodimer from CHO Conditioned Media:

CD4-gamma2 chimeric heavy chain homodimer was purified in a single step using Protein A-Sepharose® column chromatography. CHO cells secreting CD4-gamma2 chimeric heavy chain homodimer were grown to high density in roller bottles in medium containing alpha MEM with 10% IgG-free fetal calf serum. Conditioned media was collected, clarified by centrifugation, and diluted 1:1 with PBS with/or without detergent (i.e. Tween®) in this and subsequent buffers. The diluted media was then applied to a 5 ml column of Protein A-Sepharose® fast flow previously equilibrated with PBS, at a flow rate of 60 ml/hour. After extensive washing, the specifically bound material was eluted with 100 mM glycine/HCl, pH 3.5, directly into an aliquot of 1M Tris.HCl pH 8.0 to immediately neutralize the eluted fractions. The fractions were then analyzed by SDS-PAGE under reducing and non-reducing conditions followed by silver staining and pooled (FIG. 8)

The pooled fractions were then, applied to a 10 ml column of S-Sepharose® fast flow previously equilibrated with 50 mM BES pH 7.0 at a flow rate of 120 ml/hr. After application of sample, a step elution gradient (consisting of the following 4 steps: 5 column volumes of 50 mM BES pH 7.0, 4 column volumes of 50 mM BES pH 7.0, 100 mM NaCl, 6 column volumes of 50 mM BES pH 7.0, 225 mM NaCl, followed by 8 column volumes of 50 mM BES pH 7.0, 500 mM NaCl) was employed for specific elution of the CD4-gamma2 chimeric heavy chain homodimer. The CD4-gamma2 chimeric heavy chain homodimer was eluted from the column in 50 mM BES pH 7.0, 500 mM NaCl. The peak fractions were then pooled and concentrated to yield a final protein concentration of at least 1 mg/ml. The pooled and concentrated fractions were then applied to a 120 ml column of Sephacryl® S-300HR previously equilibrated with PBS, at a flow rate of 8 ml/hr. The CD4-gamma2 chimeric heavy chain homodimer fraction was specifically eluted in PBS, and concentrated to at least 1 mg/ml.

5. Demonstration of Binding of CD4-gamma2 Chimeric Heavy Chain Homodimer to the HIV Envelope Glycoprotein gp120:

CosM5 transfectants expressing CD4-gamma2 chimeric heavy chain homodimer were incubated for 72 hours in DMEM containing 10% IgG-free fetal calf serum. Unlabelled medium was then collected and used to precipitate $^{35}$S-methionine-radiolabelled HIV gp120. After incubation of CD4gamma2 chimeric heavy chain homodimer containing medium containing $^{35}$S-methionine-labelled gp120, the complexes were adsorbed to Protein A-Sepharose®. Protein A-Sepharose® complexes were recovered by centrifugation, and the precipitates were analyzed by SDS-PAGE under reducing conditions followed by fluorography (FIG. 7) Alternatively, aliquots of purified CD4-gamma2 chimeric heavy chain homodimer from CHO cells were also used to precipitate $^{35}$S-radiolabelled gp120 using the same procedure.

6. Determination of Plasma Half-Life and Placental Transfer of CD4-gamma2 Chimeric Heavy Chain Homodimer:

Determination of the plasma half-life and placental transfer are performed by well established techniques. Briefly, rabbits or monkeys are injected intravenously or intramuscularly with purified CD4-gamma2 chimeric heavy chain homodimer. At various time points post-injection, plasma samples are taken, and the quantity of the CD4-gamma2 chimeric heavy chain homodimer present in the serum is measured by ELISA. In addition, pregnant monkeys are also injected either IV or IM with CD4-gamma2 chimeric heavy chain homodimer and the concentration determined in the cord blood and the serum of the newborn monkey. Determination and comparison of the quantity of the CD4-gamma2 chimeric heavy chain homodimer in the mother's serum as well as in the cord blood and serum of the newborn indicates the relative rate of transport across the placenta of these molecules.

7. Determination of FcR Binding and Macrophage Infectivity of CD4-gamma2 Chimeric Heavy Chain Homodimer.

Determination of FcR binding and macrophage infectivity of CD4-gamma2 chimeric heavy chain homodimer are performed by well established techniques. For these studies, U937 cells (a human monocytic cell line expressing FcR1 and FcRII), purified monocyte/macrophage populations from human peripheral blood, and Hela cells constitutively expressing recombinant human FcRs are utilized. In addition, monoclonal antibodies specific for FcR1 and FcRII are commercially available. Briefly, radiolabelled monomeric or aggregated CD4-gamma2 chimeric heavy chain homodimer is incubated with the above cells and appropriate control cells at 4 degrees Celsius over various time points. At the end of each incubation, the cells are solubized and the cell-associated radioactivity is determined to establish the amount of CD4-gamma2 chimeric heavy chain homodimer specifically bound to each cell type. As controls, radiolabelled normal monomeric or aggregated human IgG2 are used to determine the levels of specific antibody binding. Furthermore, competing the radiolabelled component with unlabelled monomeric or aggregated normal human IgG2, or monoclonal antibodies to FcRI or FcRII, will establish the binding efficiency and specificity of CD4-gamma2 chimeric heavy chain homodimer to each cell type.

To ascertain whether the CD4-gamma2 chimeric heavy chain homodimer mediates enhancement of HIV infection of monocytes/macrophages, HIV-1 is incubated with media alone or either monomeric or aggregated CD4-gamma2 chimeric heavy chain homodimer at several dilutions. As controls, sera from normal individuals and HIV-infected individuals are used (31) After incubation for one hour at 4 degrees Celsius, the 'opsonized' virus is added to the cell types described in the paragraph above. At various time points after infection, the media is harvested and assayed for viral reverse transcriptase activity to determine the degree of viral infection. As controls, sCD4, OKT4a or Leu3a are included during the infection of the cells. In addition, various dilutions of the CD4-gamma2 chimeric heavy chain homodimer and appropriate controls are first incubated with the cells at 4 degress Celsius to allow binding. HIV is then added and infection assayed by viral reverse transcriptase activity.

8. HIV Binding Assay:

Binding of HIV was performed as previously described (43, 44). Briefly, concentrated HIV-1 preparations were incubated with various dilutions of sCD4, CD4-gamma2, or CD4-gamma2, for 30 minutes and then added to 5×10$^5$ CEM cells. Bound virus was detected by indirect immunofluorescence and cytofluorography as previously described (44).

9. Neutralization Assay:

The microculture assay for productive viral-replication was as previously described (43, 45). Briefly, dilutions of sCD4, CD4-gamma2, or CD4-gamma2 were incubated for 30 minutes with 100 $TCID_{50}$ HIV-1 at room temperature. The mixtures were added to PHA-stimulated lymphocytes and incubated at 37° C. overnight. The cells were then washed and plated in microculture at 1×10$^5$ cells/culture; and 10 cultures per dilution were monitored for reproductive viral replication by detection of HIV antigen in culture supernates 8 and 12 days later.

B. Construction of CD4-IgG2 Chimeric Heavy Chain and CD4-kappa Chimeric Light Chain for Expression of CD4-IgG2 Chimeric Heterotetramer:

1. Introduction

This invention describes a CD4-gamma2 chimeric heavy gene encoding a CD4-gamma2 chimeric heavy chain homodimer which is efficiently secreted from transformed mammalian cells. This chimeric molecule was designed to contain sequences from the human IgG2 heavy chain which allow for efficient homodimer assembly and secretion. The CH1 region of the IgG heavy chains is responsible for retaining heavy chain molecules intracellularly and for formation of heterotetramers with light chains (25). In order to efficiently produce CD4-gamma2 chimeric heavy chain homodimers, the CD4-gamma2 chimeric heavy chain gene described above specifically lacks the CH1 domain. The resulting homodimer contains two CD4 V1V2 moieties and therefore has the potential of being bivalent with respect to gp120 binding and having enhanced avidity for HIV compared to sCD4.

In addition, this invention describes the construction of CD4-IgG2 chimeric-heterotetramers which contain two heavy chains and two light chains. The resulting heterotetramer, containing two or four CD4 V1V2 moieties, and has the potential of being tetravalent with respect to gp120 binding and having enhanced avidity for HIV compared to sCD4. The CD4-IgG2 chimeric heavy chain gene used to produce CD4-IgG2 chimeric heterotetramer contains the entire heavy chain constant region, including the CH1 domain. The inclusion of the CH1 domain facilitates efficient intracellular association with light chains, affording the potential for secreted, disulfide-bonded heterotetramers. Both the CD4-IgG2 chimeric heavy chain gene and the CD4-kappa chimeric light chain gene contain the V1V2 domains of CD4. Efforts to express CD4-IgG2 chimeric heavy chains or CD4-kappa chimeric light chains (either alone or in combination) containing only the V1 domain of CD4 were unsuccessful.

2. Construction of CD4-IgG2 Chimeric Heavy Chain Expression Vector and CD4-kappa Chimeric Light Chain Expression Vector for Production of CD4-IgG2 Chimeric Heterotetramers.

a. Construction of CD4-IgG2 Chimeric Heavy Chain Mammalian Expression Vector.

The human CD4 cDNA sequence is excised from the plasmid pSP6T4 (4) as an EcoR1/Stu1 restriction fragment. The 0.70 kilobase fragment is isolated and cloned into EcoR1/Sma1-digested M13mp18. The resulting vector (M13mp18(CD4)) is then isolated and digested with BamH1. The BamH1 sites of the M13mp18(CD4) are made flush ended with the Klenow fragment of DNA polymerase 1. After heat inactivation of the polymerase for 15 minutes at 65 degrees Celsius, the linearized M13mp18(CD4) vector is then digested with Pst1 and purified.

In order to excise a fragment containing the CH1 exon of the human gamma2 heavy chain gene, the plasmid pBr gamma2 (36) is digested with SacII, and the SacII sites are then made flush using T4 DNA polymerase. After heat inactivation of the polymerase, the fragment is then digested with Pst1. The resulting SacII(flush)-Pst1 fragment containing the CH1 exon is then purified and ligated to the M13mp18(CD4) vector described in the above paragraph. After transformation of competent TG1 cells, the resulting recombinants are screened by restriction analysis for the presence of both CD4 and CH1 sequences which contain in tandem CD4 (EcoR1/Stu1)-CH1 (SacII(flush)/Pst1) Oligonucleotide-mediated site-directed mutagenesis is then performed to juxtapose the CD4 and CH1 sequences in frame. The resulting chimeric DNA molecule contains the V1V2 domains of CD4 fused to the CH1 domain of gamma2 heavy chain. Mutagenesis is performed on singlestranded DNA isolated from recombinant phage from transformed TG1cells (Amersham). Template DNA is annealed with a 33-mer oligonucleotide (5'-GGGCCCTTGGTGGAGGC-GAAAGCTAGCACCACG-3') containing sequences which join the last codon encoding Phe (179) from V1V2 of CD4 to the first codon of the CH1 domain for gamma2 heavy chain (encoding Ala). After second strand synthesis, double stranded DNA is transformed into competent TG1 cells. Isolated plaques are then grown in fresh TG1 cells and single-stranded DNA is purified for DNA sequencing. All mutations are confirmed by dideoxy sequencing using the Sequenase® system (USB) Plaques containing the chimeric genes with the correct sequence as determined by restriction analysis are then grown in TG1 cells, and the Rf DNA is isolated from the cells.

Figure 2A:
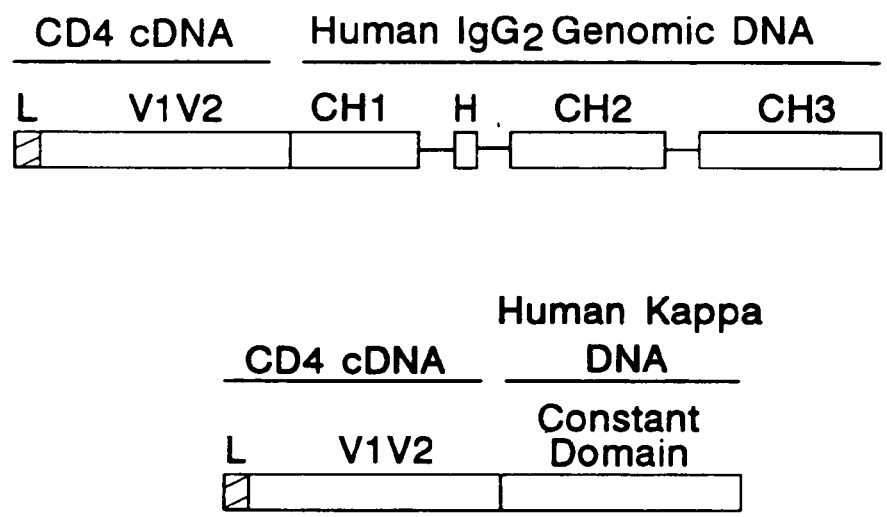
Figure 2B:
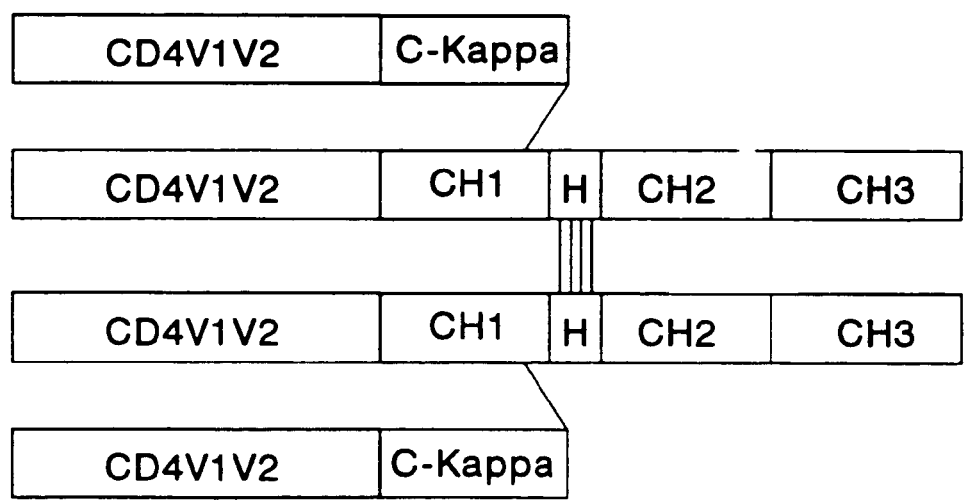

Rf DNA from the CD4-CH1 chimeric gene is then linearized by digestion with Pst1. The Pst1 linearized vector is then BAP treated and ligated to the Pst1—Pst1 DNA fragment of the plasmid pBr gamma2 containing the hinge, CH2, and CH3 exons of the human gamma2 heavy chain gene. The correct orientation of the Pst1—Pst1 fragment with respect to the chimeric CD4-CH1 fragment is then verified by restriction analysis. The resulting chimeric gene encodes a protein containing the V1V2 domains of CD4 followed by the CH1, hinge, CH2, and CH3 regions of gamma2 heavy chain (FIGS. 2A, 2B, and 4).

The CD4-IgG2 chimeric heavy chain DNA molecule is isolated from the recombinant Rf DNA following Rf linearization with EcoR1. The EcoR1 sites in the linearized DNA are filled in with the Klenow fragment of DNA polymerase I. The flush ended DNA is then ligated overnight at 15 degrees Celsius with T4 DNA ligase to a 100-fold molar excess of HindIII linkers. After heat inactivation of T4 DNA ligase for 15 minutes at 70 degrees Celsius, the HindIII-linkered DNA is extensively digested with HindIII to liberate a fragment containing the CD4-IgG2 chimeric heavy chain gene. This HindIII fragment is then purified and ligated to the expression vector pcDNA-1 (Invitrogen), which was previously digested with HindIII and BAP treated. The resulting plasmid is then transformed into MC1061/P3 cells. Plasmid DNA is isolated from recombinant clones, and verification of the presence of the HindIII insert and orientation of the insert with respect to the cytomegalovirus (CMV) promoter in the plasmid is made by restriction analysis. The resulting mammalian expression plasmid which encodes a CD4-IgG2 chimeric heavy chain is designated CD4-IgG2HC-pRcCMV.

b. Construction of a CD4-kappa Chimeric Light Chain Mammalian Expression Vector:

The human kappa light chain constant region is excised from the plasmid pCNkappa light as an Mse1 fragment. The purified Mse1 fragment is then made flush ended using the Klenow fragment of DNA polymerase 1. M13mp18 Rf is then linearized with HincII, and the flush ended Mse1 kappa light chain fragment is ligated to M13mp18 at the flush ended HincII site in the vector. After transformation of TG1 cells, the recombinants are confirmed for the presence of the insert and the correct orientation within the vector by restriction analysis. Rf is purified from infected TG1 cells and digested with EcoR1 and Sma1. The purified vector containing the kappa light chain constant region is then ligated to the EcoR1/Stu1 fragment of the human CD4 cDNA described above. The resulting recombinants are then verified for the presence and orientation of both inserts containing in tandem CD4 (EcoR1/Stu1)-Ckappa (MseI (flush)/MseI(flush)), and single-stranded DNA is purified for oligonucleotide-mediated site directed mutagenesis. Template DNA is annealed to a 33-mer oligonucleotide (5'-GATGGTGCAGCCACAGTGAAAGCTAGCACCACG-3' SEQ ID NO. 10) containing sequences which join the last codon encoding Phe(179) from V1V2 of CD4 to the first codon of the kappa light chain constant domain (encoding thr). After second strand synthesis, double-stranded DNA is transformed into competent TG1 cells, and isolated plagues are grown in fresh TG1 cells for DNA sequencing. The presence of the mutation is confirmed by dideoxy sequencing. Plaques containing chimeric genes with the correct sequence are then grown in TG1 cells, and Rf DNA is isolated from the cells. The resulting DNA molecule encodes a protein containing the V1V2 domains of CD4 followed by the constant region of kappa light chains (FIGS. 2A, 2B and 5).

The CD4-kappa chimeric light chain DNA molecule is isolated from the recombinant Rf DNA following Rf linearization with EcoR1. The EcoR1 sites in the linearized DNA are filled in with the Klenow fragment of DNA polymerase I. The flush ended DNA is, then ligated overnight at 15 degrees Celsius with T4 DNA ligase to a 100-fold molar excess of HindIII linkers. After heat inactivation of T4 DNA ligase for 15 minutes at 70 degrees Celsius, the HindIII linkered DNA is extensively digested with HindIII to liberate a fragment containing the CD4-kappa chimeric light chain gene. This HindIII fragment is then purified and ligated to the expression vector pcDNA-1 (Invitrogen), which was previously digested with HindIII and BAP treated. The resulting plasmid is then transformed into MC1061/P3 cells. Plasmid DNA is isolated from recombinant clones, and verification of the presence of the HindIII insert and orientation of the insert with respect to the cytomegalovirus (CMV) promoter in the plasmid is made by restriction enzyme analysis. The resulting mammalian expression plasmid which encodes a CD4-kappa chimeric light chain is designated CD4-kLC-pRcCMV.

3. Co-Expression of CD4-IgG2HC-pRcCMV and CD4-kLC-pRcCMV in Mammalian Cells to Produce CD4-IgG2 Chimeric Heterotetramer.

a. Transient Expression.

CosM5 cells grown in DMEM containing 10% fetal calf serum are split to 75% confluence. On the following day, the cells are transfected for 16–20 hours with 5 micrograms of CsCl purified CD4-IgG2HC-pRcCMV DNA and 5 micrograms of CsCl-purified CD4-kLC-pRcCMV plasmid DNA by the standard CaPO(4) precipitation technique. After transfection, fresh medium is added to the cells. Analysis of the products synthesized 48–72 hours post-transfection is performed by radiolabelling of transfectants with $^{35}$S-methionine for 12–18 hours followed by precipitation of media and cell lysates using anti-CD4 antibodies or by incubation with Protein A-sepharose beads alone followed by SDS-PAGE under reducing or non-reducing conditions. In addition, analysis of media and cell lysates is performed 48–72 hours post-transfection by standard Western blotting procedures.

b. Stable Expression.

Dhfr-Chinese hamster ovary cells (CHO) are transfected with 20 micrograms of CsCl purified DNA in a ratio of 1000:1000:1 CD4-IgG2HC-pRcCMV:CD4-kLC-pRcCMV: p410 (p410 is an expression plasmid containing the dhfr gene), although other ratios may also be used. At approximately 3–5 days post-transfection, cells are placed in selective medium (nucleoside-free alpha MEM containing 10% dialyzed fetal calf serum). At approximately 10–15 days post-selection, individual cell clones are picked. The clones are then analyzed for stable expression of CD4-IgG2 chimeric heterotetramers by several screening techniques, such as ELISA and precipitation with Protein A-sepharose beads followed by SDS-PAGE under reducing or non-reducing conditions. Clones expressing the highest levels are subjected to successive rounds of amplification of the newly introduced DNA sequences in increasing concentrations of methotrexate. Stable CHO cell lines are thus generated which secrete high levels of CD4-IgG2 chimeric heterotetramer.

4. Purification of CD4-IgG2 Chimeric Heterotetramers from CHO Conditioned Media:

CD4-IgG2 chimeric heterotetramers are purified using Protein A-Sepharose® column chromatography. CHO cells secreting CD4 IgG2 chimeric heterotetramers are grown to high density in roller bottles in medium containing alpha MEM with 10% IgG-free fetal calf serum. Conditioned media is collected, clarified by centrifugation, and diluted 1:1 with PBS with/or without detergent (i.e. Tween®) in this and subsequent buffers. The diluted media is then applied to a 5 ml column of Protein A-Sepharose® fast flow previously equilibrated with PBS, at a flow rate of 60 ml/hour. After extensive washing, the bound material is eluted with 100 mM glycine/HCl, pH 3.5, directly into an aliquot of 1M Tris.HCl pH 8.0 to immediately neutralize the eluted fractions. Fractions are then analyzed by SDB-PAGE under reducing and non-reducing conditions followed by silver staining and pooled (FIG. 8).

5. Demonstration of Binding of CD4-IgG2 gamma2 Chimeric Heterotetramer to the Envelope Glycoprotein gp120:

CosM5 transfectants expressing CD4-IgG2 chimeric heterotetramers are incubated for 72 hours in DMEM containing 10% IgG-free fetal calf serum. Unlabelled medium is then collected and used to precipitate $^{35}$S-methionine-radiolabelled HIV gp120. After incubation of CD4-IgG2 chimeric heterotetramer containing medium with $^{35}$S-methionine-labelled gp120, the complexes are adsorbed to Protein A-Sepharose®. Protein A-Sepharose® complexes are recovered by centrifugation, and the precipitates are analyzed by SDS-PAGE followed by fluorography. Alternatively, aliquots of purified CD4-IgG2 chimeric heterotetramers from CHO cells are alsoused to precipitate $^{35}$S-radiolabelled gp120 using the same procedure.

6. Determination of Plasma Half-Life and Placental Transfer of CD4-IgG2 Chimeric Heterotetramer:

Determination of the plasma half-life and placental transfer are performed by well established techniques. Briefly, rabbits or monkeys are injected intravenously or intramuscularly with purified CD4-IgG2 chimeric heterotetramer. At various time points post-injection, plasma samples are taken, and the quantity of the CD4-IgG2 chimeric heterotetramer present in the serum is measured by ELISA. In addition, pregnant monkeys are also injected either IV or IM with CD4-IgG2 chimeric heterotetramer and the concentration determined in the cord blood and the serum of the newborn monkey. Determination and comparison of the quantity of the CD4-IgG2 chimeric heterotetramer in the mother's serum as well as in the cord blood and serum of the newborn indicates the relative rate of transport across the placenta of these molecules.

7. Determination of FcR Binding and Macrophage Infectivity of CD4-IgG2 Chimeric Heterotetramer:

Determination of FcR binding and macrophage infectivity of CD4-IgG2 chimeric heterotetramer are performed by well established techniques. For these studies, U937 cells (a human monocytic cell line expressing FcR1 and FcRII), purified monocyte/macrophage populations from human peripheral blood, and Hela cells constitutively expressing recombinant human FcRs are utilized. In addition, monoclonal antibodies specific for FcR1 and FcRII are commercially available. Briefly, radiolabelled monomeric or aggregated CD4-IgG2 chimeric heterotetramer is incubated with the above cells and appropriate control cells at 4 degrees Celsius over various time points. At the end of each incubation, the cells are solubized and the cell-associated radioactivity is determined to establish the amount of CD4-IgG2 chimeric heterotetramer specifically bound to each cell type. As controls, radiolabelled normal monomeric or aggregated human IgG2 are used to determine the levels of specific antibody binding. Furthermore, competition of the radiolabelled component with unlabelled monomeric or aggregated normal human IgG2, or monoclonal antibodies to FcRI or FcRII, will establish the binding efficiency and specificity of CD4-IgG2 chimeric heterotetramer to each cell type.

To ascertain whether the CD4-IgG2 chimeric heterotetramer mediates enhancement of HIV infection of monocytes/macrophages, HIV-1 is incubated with media alone or either monomeric or aggregated CD4-IgG2 chimeric heterotetramer at several dilutions. As controls, sera from normal individuals and HIV-infected individuals are used (31). After incubation for one hour at 4 degrees Celsius, the 'opsonized' virus is added to the cell types described in the paragraph above. At various time points after infection, the media is harvested and assayed for viral reverse transcriptase activity to determine the degree of viral infection. As controls, sCD4, OKT4a or Leu3a are included during the infection of the cells. In addition, various dilutions of the CD4-IgG2 chimeric heterotetramer and appropriate controls are incubated first with the cells at 4 degress Celsius to allow binding. HIV is then added and infection assayed by viral reverse transcriptase activity.

B. Results

A CD4-gamma2 chimeric heavy chain gene encoding a CD4-gamma2 chimeric heavy chain homodimer was generated by ligating the leader-V1-V2 segment of the human CD4 cDNA (4) to the hinge exon of the human gamma2 heavy chain gene (30) (FIG. 1A). The resulting recombinant DNA molecule (designated CD4-IgG2-Rf) encodes the signal sequence and two amino-terminal immunoglobulin-like domains of the CD4 protein (the first 179 amino acids of mature CD4) followed by the hinge (15 amino acids), CH2 (110 amino acids), and CH3 (107 amino acids) regions of the gamma2 heavy chain protein (FIG. 3). This recombinant DNA molecule also contains two introns present within the gamma2 heavy chain gene: between the H and CH2 domains, and between the CH2 and CH3 domains. This CD4-gamma2 chimeric gene was designed to encode a CD4-gamma2 chimeric heavy chain homodimer which specifically lacks the CH1 domain of the gamma2 heavy chain. Expression of the CH1 domain without accompanying light chains prevents efficient heavy chain secretion from mammalian cells (25).

Figure 1B:
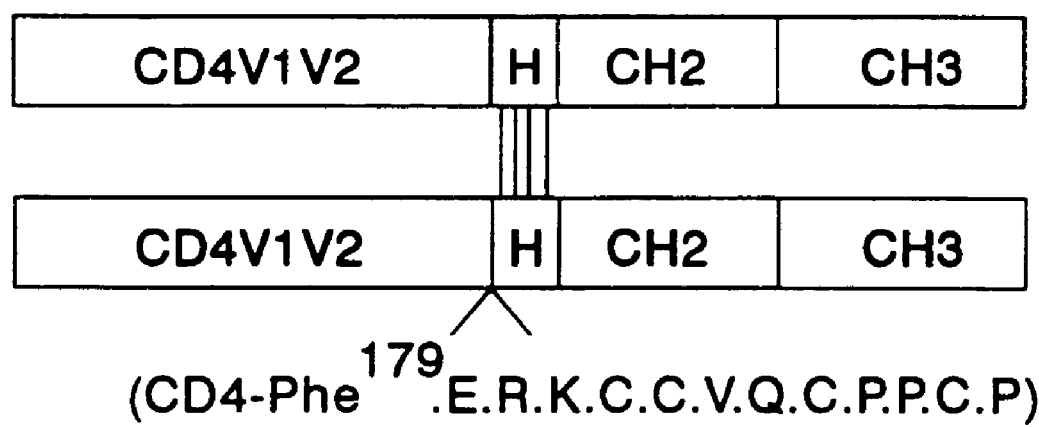

In the CD4-gamma2 chimeric heavy chain homodimer, the hinge region of one chain contains four cysteine residues, affording the potential of four interchain disulfide bonds (FIG. 1B). Similarly, naturally-occuring human IgG2 contains four interchain disulphide bonds between the gamma2 heavy chains.

The CD4-gamma2 chimeric heavy chain gene was subcloned into the mammalian expression vector pcDNA1. This vector contains the following DNA elements: the cytomegalovirus (CMV) immediate early promoter and enhancer driving transcription of the CD4-gamma2 chimeric heavy chain gene; an SV40 polyadenylation sequence; and an SV40 origin of replication which allows replication of the plasmid to high copy number in CosM5 cells. The resulting CD4-gamma2 heavy chain mammalian expression vector (designated CD4-IgG2-pcDNA1) was transfected into CosM5 cells which were then radiolabelled with $^{35}$S-methionine 48–72 hours post-transfection. The radiolabelled medium was analyzed by precipitation with Protein A-Sepharose® beads and SDS-PAGE followed by fluorography (FIG. 6). Under reducing conditions, a protein migrating at a relative molecular mass (Mr) of approximately 47 kilodaltons is precipitated. When the precipitated material was run on SDS-PAGE under nonreducing conditions, a protein migrating at an Mr of approximately 94 kilodaltons is observed, indicating that the CD4-gamma2 chimeric heavy chains assemble and are secreted as homodimers. In addition, these results demonstrate that the secreted CD4-gamma2 chimeric heavy chain homodimers contain an intact immunoglobulin Fc domain since they bind Protein A. Further characterization by Western blot analysis of the proteins secreted into the medium 48–72 hours posttransfection was performed using a rabbit polyclonal antiserum raised against purified soluble human CD4. Similar to the results obtained by precipitation, when the medium was run on SDS-PAGE under reducing conditions, followed by Western transfer to nitrocellulose, the major immunoreactive protein migrates at an Mr of approximately 47 kilodaltons. Under nonreducing conditions, the major immunoreactive protein migrates at an Mr of approximately 94 kilodaltons. Taken together, these results demonstrate that the CD4-gamma2 chimeric heavy chain is produced and secreted as a homodimer of the predicted molecular weight.

The above results demonstrate that the Fc portion of CD4-gamma2 chimeric heavy chain homodimer, encoded by the constant regions of the gamma2 heavy chain gene, binds Protein A and is therefore functionally active. In order to determine if the CD4 portion is functionally intact, CD4-gamma2 chimeric heavy chain homodimers were assayed for their ability to bind to the HIV exterior envelope glycoprotein, gp120 (FIG. 7). Unlabelled medium from CosM5 cells transfected with CD4-IgG2-pcDNA1 DNA was incubated with $^{35}$S-methionine-labelled gp120. CD4-gamma2 chimeric heavy chain homodimer/gp120 complexes were precipitated by incubation with Protein A-Sepharose® beads, and the precipitates were analyzed by SDS-PAGE under reducing conditions followed by fluorography. These results demonstrate that the CD4-gamma2 chimeric heavy chain homodimer efficiently recognizes HIV gp120 and binds with high affinity. These observations, taken together with the results described in the above paragraph, demonstrate that CD4-gamma2 chimeric heavy chain homodimer contains functionally active regions of both CD4 and gamma2 heavy chain.

In order to stably produce large quantities of the CD4-gamma2 chimeric heavy chain homodimers, the CD4-IgG2-pcDNA1 vector was cotransfected with the plasmid p410 (encoding the enzyme dihydrofolate reductase (dhfr)) into dhfr-Chinese Hamster Ovary(CHO) cells. Approximately two weeks post-transfection, individual clones growing in nucleoside free alpha MEM and 10% dialyzed fetal calf serum (and therefore dhfr+) were isolated and analyzed for co expression of CD4-gamma2 chimeric heavy chain homodimers by precipitation and ELISA. The highest producing cell lines were identified and subjected to stepwise increasing concentrations of methotrexate which selects for amplification of the newly introduced DNA sequences. A CHO cell line expressing 10 micrograms/milliliter of CD4-gamma2 chimeric heavy chain homodimer was used for stable, constitutive production in roller bottles. The cells were grown to confluence in alpha MEN containing 10% IgG-free fetal calf serum. The cells were then fed every other day and two day old conditioned medium was used for purification of the CD4-gamma2 chimeric heavy chain homodimer. Conditioned medium was diluted 1:1 with phosphate-buffered saline (PBS) and applied to a 5 ml column of Protein A-Sepharose® fast flow (Pharmacia) at a flow rate of 60 milliliters/hour. The column was then washed with 10 column volumes of PBS and the bound material was eluted with 100 mM glycine pH 3.5. The eluted material was collected directly into 50 µl of 1M Tris.HCl pH 8.0 to neutralize the eluant. Fractions having an OD(280) of greater than 0.1 were analyzed by SDS-PAGE followed by silver staining or Western blot analysis, and the peak fractions were pooled. A single band was specifically eluted from the Protein A-Sepharose® column with an Mr corresponding to the CD4-gamma2 chimeric heavy chain homodimer (FIG. 8). Western blot analysis confirms that the eluted protein is immunoreactive with polyclonal antiserum raised against soluble human CD4. In addition, the purified protein retains the ability to bind with high affinity to $^{35}$S-methionine-labelled gp120. These results demonstrate the stable, high-level production of CD4-gamma2 chimeric heavy chain homodimers in mammalian cells, and the purification of CD4-gamma2 chimeric heavy chain homodimer which retains biological function.

The partially purified CD4-gamma2 heavy chain homodimer purified as described in FIG. 8 was effective at preventing HIV binding to CD4 cells (FIG. 9) and neutralization of infectivity of a fixed HIV inoculum (FIG. 10). In this later assay, approximately 10–25 µg/ml of CD4-gamma2 as well as SCD4 were required to prevent 50% of the cultures from becoming infected by HIV.

Further purification of CD4-gamma2 heavy chain homodimer was achieved using ion-exchange chromatography. The peak fraction from the protein A-Sepharose® column was applied to a 10 ml S-Sepharose® fast flow column preequilibrated with 50 mM BES pH 7.0, at a flow rate of 120 ml/hr. After application of the sample, the column was extensively washed with 50 mM BES pH 7.0 with increasing salt concentration (see materials and methods). CD4-gamma2 heavy chain homodimer was specifically eluted from the column in 50 mM BES pH 7.0 containing 500 mM NaCl. Following the ion exchange chromatography, we unexpectedly found the peak fractions containing the CD4-gamma2 chimeric heavy chain homodimer was still impure. Therefore, the peak fractions from the S-Sepharose® column were pooled, concentrated and applied to a 120 ml Sephacryl® S-300HR column preequilibrated with PBS and run at a flow rate of 8 ml per hour. The peak fractions of purified CD4-gamma2 heavy chain homodimer were analyzed by SDS-PAGE and silver staining under non-reducing conditions, and the purified fractions were pooled and analyzed by SDS-PAGE followed by silver staining under non-reducing conditions (FIG. 11, lane 1), or reducing conditions (FIG. 11, lane 2). When the purified CD4-gamma2 chimeric heavy chain homodimer was run on SDS-PAGE under reducing conditions, a doublet was observed which appeared to be due to differences in glycosylation of the CD4-gamma2 chimeric heavy chain homodimer (data not shown).

A CD4-IgG2HC chimeric heavy chain gene encoding a CD4-IgG2 chimeric heavy chain was generated by ligating the leader-V1-V2 segment of the human CD4 cDNA to the CH1 exon of the human IgG2 heavy chain gene (FIG. 2A). In addition a CD4-kappa chimeric light chain gene encoding a CD4-kappa light chain was generated by ligating the leader-V1-V2 segment of the human CD4 cDNA to the constant domain of the kappa light chain gene (FIG. 2A). These CD4-IgG2 chimeric heavy chain genes and CD4-kappa chimeric light chain genes were designed to encode a CD4-IgG2 chimeric heterotetramer, in which the CD4-IgG2 heavy chain contains a CH1 domain for efficient association with kappa light chains.

Figure 12B:
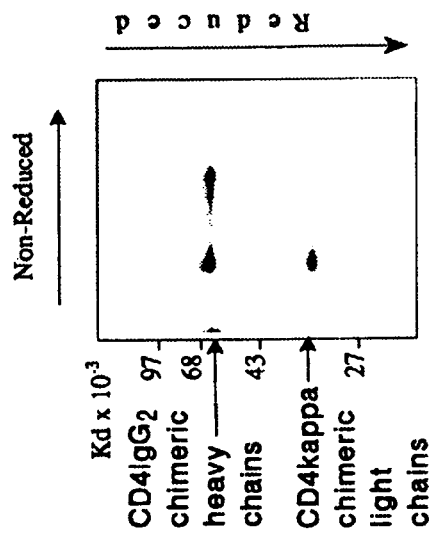
Figure 12A:
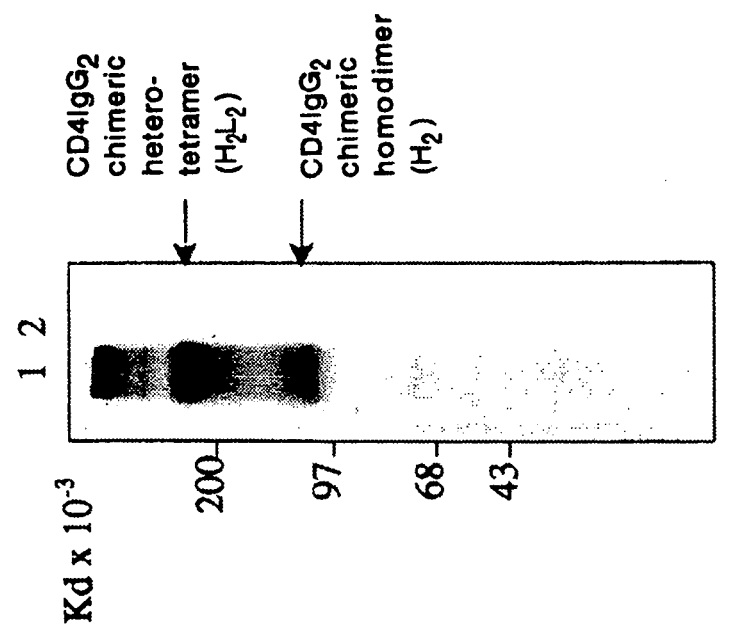

Both the CD4-IgG2 chimeric heavy chain and the CD4-kappa chimeric light chain genes were subcloned into the mammalian expression vectors pRcCMV or pPPI-2. Both vectors contain the cytomegalovirus immediate early promoter and enhancer driving transcription of the chimeric genes. In the vector pRcCMV, a second transcriptional cassette which contains the RSV promoter and enhancer is used to direct the transcription of the neomycin resistance gene. In pPPI-2, a second transcriptional cassette which contains the β-globin promoter directs the transcription of the dhfr gene (see supra). In order to stably produce large quantities of the CD4-IgG2 chimeric heterotetramer, the CD4-IgG2 chimeric heavy chain expression vector and the CD4-kappa chimeric light chain expression vector were transfected simultaneously (typically the CD4-IgG2 chimeric heavy chain gene cloned in pRcCMV was used, and CD4-kappa chimeric light chain gene cloned in pPPI-2 was used in a ratio of 1:1). Approximately two weeks post-transfection, individual clones growing in nucleoside-free alpha MEM containing 1 mg/ml G418 and 10% dialyzed fetal calf serum were isolated and analyzed for co-expression of both CD4-IgG2 chimeric heavy chains and CD4-kappa chimeric light chains by immunoprecipitation and ELISA. FIG. 12 demonstrates one clone which was selected and analyzed for the expression of both CD4-IgG2 chimeric heavy chains and CD4-kappa chimeric light chains. The CHO cell line or the untransfected parental CHO cell line was radiolabelled with $^{35}$S-methionine and $^{35}$S-cysteine for 16 hours. The radiolabelled medium was analyzed by precipitation with Protein A-Sepharose® beads and SDS-PAGE under non-reducing conditions followed by fluorography (FIG. 12A) Under nonreducing conditions 2 proteins migrating at relative molecular masses of approximately 140 kilodaltons and 210 kilodaltons are precipitated. When the precipitated material was run on SDS-PAGE under non-reducing conditions, 2 proteins migrating at relative molecular masses of 69 kilodaltons and 35 kilodaltons were observed, which are consistent with the relative predicted molecular masses of the CD4-IgG2 chimeric heavy chains, and CD4-kappa chimeric light chains respectively (data now shown). Further characterization has shown that the protein migrating at 210 kilodaltons on SDS-PAGE under non-reducing conditions contains both CD4-IgG2 chimeric heavy chains and CD4-kappa chimeric light chains which are covalently associated, while the protein migrating at 140 kilodaltons on SDS-PAGE under non-reducing conditions contains only CD4-IgG2 chimeric heavy chains (FIG. 12B) These data are consistent with the predicted molecular weight of the 210 kilodalton protein having 2 CD4-IgG2 chimeric heavy chains and 2 CD4-kappa chimeric light chains, covalently associated to form a molecule with the structure $H_2L_2$ (H=heavy chain, L=light chain) Furthermore, the 140 kilodalton protein seen on SDS-PAGE under non-reducing conditions is consistent with the predicted molecular weight of a CD4-IgG2 chimeric homodimer having the structure $H_2$. Taken together, these results indicate that a CHO cell line which expresses both CD4-IgG2 chimeric heavy chains and CD4-kappa chimeric light chains is able to efficiently assemble and secrete CD4-IgG2 chimeric heterotetramers.

REFERENCES

1. Klatzmann, D. R. et. al. (1990) Immunodeficiency Reviews 2, 43–66.
2. Lasky, L. A., et. al. (1987) Cell 50, 975–985.
3. Maddon, P. J., et. al. (1986) Cell 47, 333–348.
4. Maddon, P. J., et. al. (1985) Cell 42, 93–104.
5. Wain-Hobson, D., et. al. (1985) Cell 40, 9–17.
6. Maddon, P. J., et. al. (1987) Proc. Natl. Acad. Sci. U.S.A., 84, 9155–9159.
7. Richardson, N. E., et. al. (1988) Proc. Natl. Acad. Sci. U.S.A. 85, 6102–6106.
8. Chao, B. H., et. al. (1989) J. Biol. Chem. 264, 5812–5817.
9. Arthos, J., et. al. (1989) Cell 57, 469–481.
10. Wang, J., et al. (1990) Nature 348, 411–418.
11. Ryu, S-E., et. al. (1990) Nature 348, 419–426.
12. Maddon, P. J. et. al. (1988) PCT WO88/01304.
13. Moore, J. P., et al (1990) Science 250, 1139–1142.
14. Schooley, R. T., et. al. (1990) Ann. Internal Med. 112, 247–253.
15. Kahn, J. O., et. al. (1990) Ann. Internal Med. 112, 254–261.
16. Daar, E. S., et. al. (1990) Proc. Natl. Acad. U.S.A. 87, 6574–6578.
17. Boss, M. A., et. al. (1989) U.S. Pat. No. 4,816,397.
18. Cabilly S., et. al. (1989) U.S. Pat. No. 4,816,567.
19. Morrison, S. L. et. al. (1984) Proc. Natl. Acad. Sci. 81, 6851–6855.
20. Capon, D. J., and Gregory, T. J., (1989) PCT WO89/02922.
21. Capon, D. J., et. al. (1989) Nature 337, 525–531.
22. Byrn, R. A., et. al. (1990) Nature 344, 667–670.
23. Berger, E. A., et. al. (1990) PCT WO90/01035.
24. Seed, B., (1989) PCT WO89/06690.
25. Hendershot, L., et. al. (1987) J. Cell Biol. 104, 761–767.
26. Traunecker, A., et. al. (1989) Nature 339, 68–70.
27. Till, M., et. al. (1988) Science 242, 1166–1168.
28. Pastan, I., et. al. (1989) J. Biol. Chem. 264, 15157–15160.
29. Gartner, S., et al. (1986) Science 233, 215–219.
30. Simister, N. E., (1990) in: Fc REceptors and the Action of Antibodies, ISBN 1-55581-016-0, pp. 57–73.
31. Perno, C-F., et al (1990), J. Exp. Med. 171, 1043–1056.
32. Porterfield, J. S., et al. (1986), Adv. Virus Res. 31, 335.
33. Kabat, E., et al. (1987) in: Sequences of Proteins of Immunological Interest, 4th Edition.
34. Underdown, B. J., in: Fc Receptors and the Action of Antibodies, ISBN 1-55581-016-0, pp. 74–93.
35. Burton, D., (1985), Molecular Immunology 22, 161–206.
36. Oi, V. T., and Morrison, S. L., (1986) Biotechnology 4, 214–223.
37. Okayama, H., Mol. Cel. Biol., 3:280 (1983).
38. Remington's Pharmaceutical Science, 16th Ed., Mack Eds., 1980.
39. Duncan et al., Analy. Biochem. 132:68–73 (1983).
40. Thorpe et al., Cancer Res. 47:5924 (1987).
41. Ghotie et al., Cancer Res. 48:2610 (1988).
42. Maniatis, T., et. al., Molecular Cloning, Vol. 1–3, (1990).
43: Kennedy, M. S., et al. (1991) AIDS Res. and Human Retroviruses 7, 975–981.
44. McDougal, J. S., et al. (1986) J. Immunol 137, 2937–2944.
45. McDougal, J. S., et al. (1985) J. Immunol Methods 76, 171–183.

---

What is claimed is:

1. A transformed host cell comprising at least two vectors, one vector comprising a DNA sequence encoding heavy chains of a CD4-IgG2 chimeric heterotetramer, and one vector comprising a DNA sequence encoding light chains of the CD4-IgG2 chimeric heterotetramer, wherein the CD4-IgG2 chimeric heterotetramer comprises two heavy chains having the amino acid sequence set forth in SEQ ID NO: 4, and two light chains having the amino acid sequence set forth in SEQ ID NO: 6, and wherein the CD4-IgG2 chimeric heterotetramer produced in the cell is capable of neutralizing an HIV-1-infected individual's HIV-1 virus.

2. The transformed host cell of claim 1, wherein the cell is a mammalian cell-line cell.

3. The transformed host cell of claim 2, wherein the mammalian cell line cell is COS-7 Chinese hamster ovary-cell-DHFR or a myeloma cell.

4. The transformed host cell of claim 1, wherein the cell secretes the CD4-IgG2 chimeric heterotetramer.

5. The transformed host cell of claim 1, wherein the vector encoding heavy chains is designated CD4-IgG2HC-pRc-CMV having ATCC No. 75193.

6. The transformed host cell of claim 1, wherein the vector encoding light chains is designated CD4-kLC-pRcCMV having ATCC No. 75194.

7. The transformed host cell of claim 1, wherein the vector encoding heavy chains is designated CD4-IgG2HC-pRc-CMV having ATCC No. 75193 and the vector encoding light chains is designated CD4-kLC-pRcCMV having ATCC No. 75194.

8. The transformed host cell of claim 1, wherein the DNA sequence encoding heavy chains has the DNA sequence set forth in SEQ ID NO: 4.

9. The transformed host cell of claim 1, wherein the DNA sequence encoding light chains has the DNA sequence set forth in SEQ ID NO: 6.

* * * * *